(12) United States Patent
Humbert et al.

(10) Patent No.: US 10,538,482 B2
(45) Date of Patent: Jan. 21, 2020

(54) ADAMANTANE AND MEMANTINE DERIVATIVES AS PERIPHERAL NMDA RECEPTOR ANTAGONISTS

(71) Applicants: Institut National de la Santé et de la Recherche Médicale (INSERM), Paris (FR); Assistance Publique-Hôpitaux De Paris, Paris (FR); Centre National de la Recherche Scientifique (CNRS), Paris (FR); Université Paris-Sud, Orsay (FR)

(72) Inventors: Marc Humbert, Le Plessis-Robinson (FR); Sylvia Cohen-Kaminsky, Le Plessis-Robinson (FR); Sébastien Dumas, Leuven (BE); Gilles Bru-Mercier, Pessac (FR); Mouad Alami, Chatenay-Malabry (FR); Jean-Daniel Brion, Chatenay-Malabry (FR); Samir Messaoudi, Chatenay-Malabry (FR); Gilles Galvani, Chatenay-Malabry (FR)

(73) Assignees: Institut National de la Santé et de la Recherche Médicale (INSERM), Paris (FR); Assistance Publique-Hopitaux de Paris, Paris (FR); Centre National de la Recherche Scientifique (CNRS), Paris (FR); Université Paris-Sud, Orsay (FR)

( * ) Notice: Subject to any disclaimer, the term of this patent is extended or adjusted under 35 U.S.C. 154(b) by 0 days.

(21) Appl. No.: 15/747,507
(22) PCT Filed: Jul. 26, 2016
(86) PCT No.: PCT/EP2016/067846
§ 371 (c)(1),
(2) Date: Jan. 25, 2018
(87) PCT Pub. No.: WO2017/017116
PCT Pub. Date: Feb. 2, 2017

(65) Prior Publication Data
US 2018/0215699 A1 Aug. 2, 2018

(30) Foreign Application Priority Data

Jul. 28, 2015 (EP) .................................... 15306228

(51) Int. Cl.
| | | |
|---|---|---|
| *C07C 211/62* | (2006.01) | |
| *C07C 215/08* | (2006.01) | |
| *C07C 251/38* | (2006.01) | |
| *C07C 211/63* | (2006.01) | |
| *A61P 9/12* | (2006.01) | |

(52) U.S. Cl.
CPC .............. *C07C 211/62* (2013.01); *A61P 9/12* (2018.01); *C07C 211/63* (2013.01); *C07C 215/08* (2013.01); *C07C 251/38* (2013.01); *C07C 2601/02* (2017.05); *C07C 2601/08* (2017.05); *C07C 2601/14* (2017.05); *C07C 2603/74* (2017.05)

(58) Field of Classification Search
CPC . C07C 211/62; C07C 211/63; C07C 2601/14; C07C 2601/08; C07C 2601/02; C07C 251/38; C07C 2603/74; A61P 9/12
See application file for complete search history.

(56) References Cited

U.S. PATENT DOCUMENTS

| | | | |
|---|---|---|---|
| 4,665,110 A | 5/1987 | Zones | |
| 5,256,391 A | 10/1993 | Chen | |
| 5,576,355 A | 11/1996 | Chen | |
| 7,619,007 B2 * | 11/2009 | Went | ...................... A61K 31/13 |
| | | | 514/662 |

FOREIGN PATENT DOCUMENTS

| | | |
|---|---|---|
| CN | 101565375 A | 10/2009 |
| CN | 103420853 A | 12/2013 |
| WO | WO 2015105195 A1 | 7/2015 |

OTHER PUBLICATIONS

Bityukova et al., *Anticholinesterase Activity of Monoquaternary Ammonium Salts Containing Hydrophobic Radicals*, 22(6) Khimiko-Farmatsevticheskii Zhurnal 686-691 (1988) (translation Plenum Publishing Corporation, NY, 452-456 (1989)).
Bolshakov et al., *Different arrangement of hydrophobic and nucleophilic components of channel binding sites in N-Methyl-$_D$-aspartate and AMPA receptors of rat brain is revealed by channel blockade*, 291 Neuroscience Letters 101-104 (2000).
Bolshakov et al., *Design of antagonists for NMDA and AMPA receptors*, 49 Neuropharmacology 144-155 (2005).
Burckbuchler et al., *Development and Characterization of New Cyclodextrin Polymer-Based DNA Delivery Systems*, 19 Bioconjugate Chem. 2311-2320 (2008).
Chakrabarti et al., *Reconfigurable Four-Component Molecular Switch Based on pH-Controlled Guest Swapping*, 9(12) Organic Letters 2349-2352 (2007).
Guo et al., *Synthesis of novel quaternary ammonium surfactants containing adamantane*, 23 Chinese Chemical Letters 653-656 (2012).
Klimova et al., *Synthesis of 1-Aminoadamantane Derivatives*, 4(11) Khimiko-Farmatsevticheskii Zhurnal 14-18 (1970) (translation Plenum Publishing Corporation, NY, 609-613 (1971)).

* cited by examiner

*Primary Examiner* — Alexander R Pagano
*Assistant Examiner* — Ebenezer O Sackey
(74) *Attorney, Agent, or Firm* — Buchanan Ingersoll & Rooney PC

(57) ABSTRACT

The present invention relates to cationic compounds of formula (I) for use as peripheral NMDA receptor antagonists.

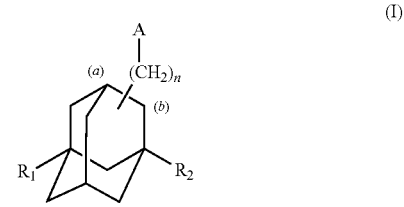

16 Claims, 1 Drawing Sheet

ADAMANTANE AND MEMANTINE DERIVATIVES AS PERIPHERAL NMDA RECEPTOR ANTAGONISTS

CROSS-REFERENCE TO RELATED APPLICATIONS

Figure 1:
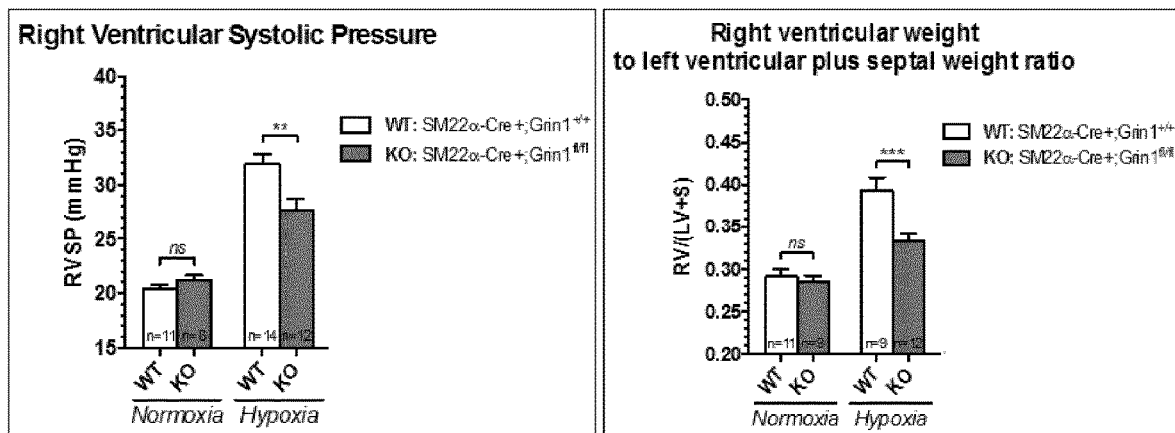

This application is a U.S. National Stage Application pursuant to 35 U.S.C. § 371 of International Patent Application PCT/EP2016/067846, filed on Jul. 26, 2016, and published as WO 2017/017116 on Feb. 2, 2017, which claims priority to European Patent Application 15306228, filed on Jul. 28, 2015, all of which are incorporated herein by reference in their entireties for all purposes.

The present invention relates to the identification of novel adamantine and memantine derivatives and to the use of such compounds as peripheral NMDA (N-Methyl-D-Aspartate) receptor antagonists in particular for the treatment of pulmonary hypertension (PH), and preferably for the treatment of pulmonary arterial hypertension (PAH).

Pulmonary hypertension defines a group of clinical conditions presenting with abnormal elevation in the pulmonary circulation pressure. Thus, a normal mean pulmonary artery pressure (mPAP) at rest is 14±3.3 mm Hg, and a PH is commonly defined as an increase of mPAP≥25 mm Hg at rest, as assessed by right heart catheterization. The PH diseases are classified into five classes: class 1 to class 5 (*Management of pulmonary arterial hypertension*. McLaughlin V. V., Shah 5.1, Souza R., Humbert M., *J. Am. Coll. Cardiol.*, 2015 May 12; 65(18):1976-97). In particular, pulmonary hypertension diseases include pulmonary arterial hypertension (group 1), such as pulmonary veno-occlusive disease and/or pulmonary capillary hemangomatosis, PH due to left heart disease (group 2), PH due to lung diseases and/or hypoxia (group 3), chronic thromboembolic pulmonary hypertension (group 4), and other PH conditions with unclear multifactorial mechanisms (group 5).

Among pulmonary hypertension diseases, the pulmonary arterial hypertension is a devastating pulmonary vascular disease causing breathlessness, loss of exercise capacity and ultimately death. As recently, pointed by the inventors, this disease is characterized by a chronic increase in pulmonary artery pressure (above 25 mmHg), caused by an important remodeling of small pulmonary vessels associated to inflammation, leading to progressive vessel occlusion, ultimately leading to right ventricular failure and death (Cohen-Kaminsky S et al., *Drug Discovery Today* 2014, Huertas A, et al., *Circulation*, 2014).

There is unfortunately no cure of PAH. The current PAH therapies are essentially focused on decreasing pulmonary vascular resistance by stimulating pulmonary vasodilation (prostacyclin analogues, phosphodiesterase type 5 inhibitors, and endothelin receptor antagonists) (Humbert et al., *N. Engl. J. Med.* 2004, O'Callaghan D S, et al. *Nat. Rev. Cardiol.*, 2014). These agents have some anti-remodeling properties, but there is no current anti-remodelling strategy approved for PAH. In spite of these treatments targeting endothelial cell dysfunction that are now available to improve quality of life and survival, in most patients the outcome is very poor. Median survival of PAH (that was 2.8 years in the 1980's) remains inferior to 5 years and refractory cases are candidates for heart-lung transplantation, a major surgery with current limitations due to shortage of organ donors and severe long-term complications (5-year survival is only 50%). Some hemodynamic and clinical effects of the tyrosine kinase inhibitor imatinib have also been reported in severe PAH, but at the expense of severe side effects.

Therefore, the discovery of new treatments targeting other PAH pathomechanisms would be useful to slow, stop, or even reverse disease progression.

In PAH, right heart failure is secondary to extensive remodeling and progressive obstruction of small pulmonary vessels, a complex and multifactorial process involving uncontrolled smooth muscle cell proliferation. Endothelial cell dysfunction is thought to mediate structural changes in the pulmonary vasculature, yet it is increasingly evident that inflammation plays a role in PAH pathogenesis (Price et al., *Chest*, 2012). It has been established that i) inflammation influences vascular remodeling and (ii) immune dysfunction and autoimmunity may contribute to the pathophysiology of PAH (Perros et al., *Am. J. Respir. Crit. Care Med.* 2012, *Med. Sci.* 2013, *Am. J. Respir. Crit. Care Med.*, 2013).

Recently, the inventors of the present invention demonstrated that NMDA receptors contributes to pulmonary remodeling and thus, have a role in the development of pulmonary hypertension.

It is reminded that the NMDA receptor has been first discovered in the central nervous system (CNS) playing a role in neurotransmission, neuronal plasticity and learning and memory. In addition it is involved in neurodegenerative diseases, such as Alzheimer disease and stroke.

More precisely, NMDA receptor (NMDAR) is a specific type of ionotropic glutamate receptor with a high permeability to calcium and a unique feature of controlling numerous calcium-dependent processes, such as cell proliferation. Functional NMDA receptors are tetrameric assemblies composed of multiple GluN1 subunits in combination with at least one type of GluN2 to generate a large number of different NMDARs.

One way in which the functions of the various NMDAR subunits may be assessed is through the use of subunit selective agonists and antagonists and a number of pharmacological agents have already been shown to distinguish between certain NMDAR subtypes. Memantine, MK-801, dextrophan, aptiganel, ifenprodil, Ro-25-6981 are for example representative NMDAR antagonists.

Several studies described the use of adamantine derivatives as NMDA receptor antagonists (Bolshakov et al., *Neuropharmacology*, 2005, vol. 49, pages 144-145 and Bolshakov et al., *Neuroscience Letters*, 2000, vol. 291, pages 101-104). The described compounds play a role inside the CNS.

It is now known that NMDARs also play a role outside the CNS in various peripheral systems, including bone, pancreas and skin, where they play important functions such as regulation of the bone mass, liberation of insulin and skin development (Skerry T M, Genever P G. *Trends Pharmacol. Sci.*, 2001), and kidney function (Dryer S, *Nephrol. Dial. Transplant.*, 2015). The expression of NMDA receptors has also been characterized in the peripheral tissues, including the lung, the heart and the immune system.

At last, several studies have shown the utility of NMDA receptor antagonists to limit tumor growth (Takano T et al., *Nature Medicine*, 2001, Rothstein J D et al., *Nature Medicine*, 2001, Rzeski W et al., *PNAS*, 2001). However, NMDA receptor expression is not limited to glioblastoma and many tumors may express NMDA receptors.

Thus, NMDARs have a preeminent role in many physiological and pathological processes outside the CNS.

However, at the knowledge of the inventors there is no information available about the development of peripheral NMDAR antagonists.

Otherwise, since the NMDA receptor has been first discovered in the CNS, the available NMDA receptor blockers, like in particular memantine and ifenprodil, are essentially provided as neuroprotective drugs that are useful in stroke, traumatic brain injury, epilepsy, Alzheimer disease, Parkinson disease, Huntington's chorea, and others involving the brain and or the spinal cord tissue.

Accordingly, NMDA receptor blockers produced so far are mainly designed and used with the intention that they will cross the blood brain barrier in order to treat neurological diseases.

Unfortunately, general blocking of NMDA receptors that could reach the brain causes adverse effects such as ataxia, memory deficit, hallucination, cognitive disruption, psychotic-spectrum reaction and other neurological problems. One of these antagonists Dizocilpine (MK-801) is even used in an animal model to mimic psychosis for experimental purposes and it also induces brain lesions called Olney's lesions, in test rats.

Thus, to date, most NMDAR antagonists that reached clinical development to treat neurodegenerative diseases cannot be used in the periphery without major central side-effects.

Indeed, it is not acceptable to use such drugs for treating a chronic disease with peripheral NMDAR involvement, such as pulmonary hypertension and in particular pulmonary arterial hypertension with secondary deleterious toxic side effects on healthy brain tissues.

Therefore, there is a crucial need for new peripheral NMDAR blockers.

In particular, there is a need for new compounds selectively targeting the peripheral NMDA receptor but not crossing the blood brain barrier. However, a minimized brain penetration to reduce undesirable CNS side-effects has not to be obtained in detriment of the expected peripheral NMDARs blocking activity.

Furthermore, there is a need for new compounds acting as selective antagonists toward NMDARs, not crossing the blood-brain barrier and having a good aqueous solubility to be convenient at least for administration.

More particularly, there is a need to provide new means of treating a disease with peripheral NMDAR involvement, such as pulmonary hypertension and in particular pulmonary arterial hypertension.

The present invention precisely aims to provide novel compounds complying with the previous requirements.

Therefore, according to one of its aspects, the invention is directed to cationic compounds of formula (I):

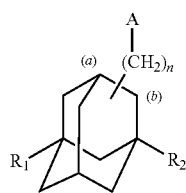

(I)

wherein:
R$_1$ and R$_2$ represent, independently of each other, a hydrogen atom or a (C$_1$-C$_6$)alkyl group;
the group —(CH$_2$)$_n$-A is linked to the cycle in position (a) or (b);
n is 0, 1, 2 or 3;
A represents a —NR$_3$R$_4$ group or a —N$^+$R$_3$R$_4$R$_5$ group;
R$_3$, R$_4$ and R$_5$ represent, independently of each other, a hydrogen atom, a (C$_1$-C$_{10}$)alkyl group, a (C$_1$-C$_{10}$)alkoxy group, a (C$_1$-C$_{10}$)alkyl-C(=NH)(—OH) group, a (C$_3$-C$_8$)cycloalkane group, a 6- to 10-membered aryl group or a 5- to 12-membered heteroaryl group; said alkyl or alkoxy groups being optionally substituted with one or more —NR$_6$R$_7$ group, —N$^+$R$_6$R$_7$R$_8$ group, (C$_3$-C$_8$)cycloalkane group, 6- to 10-membered aryl group or 5- to 12-membered heteroaryl group;
with R$_6$, R$_7$ and R$_8$ represent, independently of each other, a hydrogen atom or a (C$_1$-C$_6$)alkyl; and
the compound of formula (I) contains at least one positive charged nitrogen atom, provided that R$_1$ and R$_2$ are not both a hydrogen atom; and
provided that when R$_1$ and R$_2$ are a methyl group, the group —(CH$_2$)$_n$-A is linked to the cycle in position (a), and n is 0, then A is not a group —N$^+$H$_3$.

It is understood that when A represents a —N$^+$R$_3$R$_4$R$_5$ group, then R$_3$, R$_4$ and R$_5$ cannot represent a hydrogen atom.

Furthermore, it is understood that when at least one of R$_3$, R$_4$ or R$_5$ represents an alkyl or alkoxy group substituted with at least one —N$^+$R$_6$R$_7$R$_8$ group, then R$_6$, R$_7$ and R$_8$ cannot represent a hydrogen atom.

According to another of its aspects, the present invention also relates to cationic compounds of general formula (I) as defined above for use as a peripheral NMDA receptor antagonist.

Within the meaning of the invention, the term "peripheral NMDA receptor antagonist" is intended to mean an antagonist playing a role outside the CNS in various peripheral systems, for example the peripheral tissues, including the lung, the heart and the immune system. More specifically, the term "peripheral NMDA receptor antagonist" relates to both neuronal and non-neuronal peripheral NMDAR expressed outside the CNS.

The invention also describes compounds of formula (I):

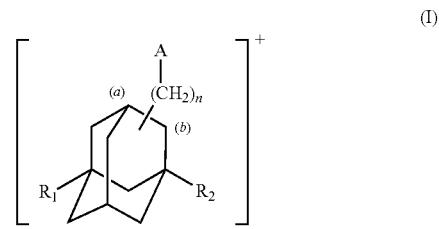

(I)

wherein:
R$_1$ and R$_2$ represent, independently of each other, a hydrogen atom or a (C$_1$-C$_6$)alkyl group;
the group —(CH$_2$)$_n$-A is linked to the cycle in position (a) or (b);
n is 0, 1, 2 or 3;
A represents a —NR$_3$R$_4$ group or a —N$^+$R$_3$R$_4$R$_5$ group;
R$_3$, R$_4$ and R$_5$ represent, independently of each other, a hydrogen atom, a (C$_1$-C$_{10}$)alkyl group, a (C$_1$-C$_{10}$)alkoxy group, a (C$_1$-C$_{10}$)alkyl-C(=NH)(—OH) group, a (C$_3$-C$_8$)cycloalkane group, a 6- to 10-membered aryl group or a 5- to 12-membered heteroaryl group; said alkyl or alkoxy groups being optionally substituted with one or more —NR$_6$R$_7$ group, —N$^+$R$_6$R$_7$R$_8$ group, (C$_3$-C$_8$)cycloalkane group, 6- to 10-membered aryl group or 5- to 12-membered heteroaryl group;

with $R_6$, $R_7$ and $R_8$ represent, independently of each other, a hydrogen atom or a ($C_1$-$C_6$)alkyl; and the positive charge of the compound being carried by at least a nitrogen atom, for use as a peripheral NMDA receptor antagonist.

As detailed here-after, the inventors identified some chemical modifications which, when introduced in the parent molecule memantine or adamantine, allow to achieve compounds, that are advantageously unable to cross the blood brain barrier but still exhibit a selective and efficient peripheral NMDARs blocking activity.

As shown in the following examples, compounds according to formula (I) may advantageously have a Kp brain value measured in rat, lower than 0.1 by contrast to memantine which has a Kp brain value of 31.6.

It is reminded that in vivo equilibrium distribution between blood and brain in rodents is the most commonly used parameter to evaluate brain penetration. This parameter is defined as the ratio of concentrations in brain and blood, $Kp_{\text{``brain''}} (C_{brain}/C_{plasma})$ or log(BB).

Log(BB) is the logarithm of the ratio of the steady-state total concentration of a compound in the brain to that in the blood/plasma, $\log(BB)=\log(C_{brain}/C_{plasma})$.

This parameter depends upon the passive diffusion characteristics, the implication of membrane transporters at the blood brain barrier (BBB) level and the relative drug binding affinity differences between the plasma proteins and brain tissue.

Generally, compounds with a brain/plasma ratio of greater than 0.3-0.5 are considered to have sufficient access to the central nervous system (CNS), compounds with a value greater than 1 freely cross the BBB, whereas compounds with a brain/plasma ratio smaller than 0.1 may be unable to enter the CNS. As shown in the following example 3, claimed compounds do not penetrate the central nervous system (CNS) in rat.

Thus, this property of not crossing the BBB is advantageously not deleterious for the expected selective peripheral NMDARs blocking activity.

Accordingly, the compounds according to the invention may be used as selective peripheral NMDA receptor antagonist for treating, without central side-effects, the conditions and diseases with peripheral NMDA receptors involvement. Advantageously, they target peripheral NMDARs in the three systems (cardiac, pulmonary, immune), notably involved in PH, and in particular in PAH, without central side-effects.

According to the invention, the term "central side-effects" encompasses adverse effects in particular on healthy brain tissues, such as ataxia, memory deficit, hallucination, cognitive disruption, psychotic-spectrum reaction and other neurological problems.

The present invention also describes compounds of general formula (I):

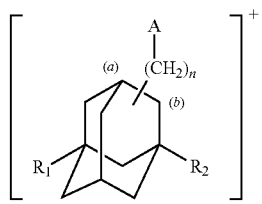

(I)

wherein:
$R_1$ and $R_2$ represent, independently of each other, a hydrogen atom or a ($C_1$-$C_6$)alkyl group;

the group —$(CH_2)_n$-A is linked to the cycle in position (a) or (b);

n is 0, 1, 2 or 3;

A represents a —$NR_3R_4$ group or a —$N^+R_3R_4R_5$ group;

$R_3$, $R_4$ and $R_5$ represent, independently of each other, a hydrogen atom, a ($C_1$-$C_{10}$)alkyl group, a ($C_1$-$C_{10}$)alkoxy group, a ($C_1$-$C_{10}$)alkyl-C(=NH)(—OH) group, a ($C_3$-$C_8$)cycloalkane group, a 6- to 10-membered aryl group or a 5- to 12-membered heteroaryl group; said alkyl or alkoxy groups being optionally substituted with one or more —$NR_6R_7$ group, —$N^+R_6R_7R_8$ group, ($C_3$-$C_8$)cycloalkane group, 6- to 10-membered aryl group or 5- to 12-membered heteroaryl group;

with $R_6$, $R_7$ and $R_8$ represent, independently of each other, a hydrogen atom or a ($C_1$-$C_6$)alkyl; and the positive charge of the compound being carried by at least a nitrogen atom;

provided that when $R_1$ and $R_2$ are a hydrogen atom, the group —$(CH_2)_n$-A is linked to the cycle in position (a) or (b), and n is 0, then A is not a group —$N^+H_3$ or —$N^+(CH_3)_3$ or —$N^+(CH_3)_2(CH_2CH_3)$; and provided that when $R_1$ and $R_2$ are a methyl group, the group —$(CH_2)_n$-A is linked to the cycle in position (a), and n is 0, then A is not a group —$N^+H_3$.

As mentioned above, it is understood that when A represents a —$N^+R_3R_4R_5$ group, then $R_3$, $R_4$ and $R_5$ cannot represent a hydrogen atom, and when at least one of $R_3$, $R_4$ or $R_5$ represents an alkyl or alkoxy group substituted with at least one —$N^+R_6R_7R_8$ group, then $R_6$, $R_7$ and $R_8$ cannot represent a hydrogen atom.

According to another of its aspects, the invention is directed to compounds of formula (I) according to the invention for use for preventing and/or inhibiting and/or treating a disease or a condition in which the peripheral NMDA receptors are involved, like pulmonary hypertension diseases and in particular pulmonary arterial hypertension.

According to the present invention, pulmonary hypertension diseases cover any pathologies trouble commonly identified under that name. According to this aspect, the present invention also covers any new group or subgroup of pulmonary arterial hypertension and pulmonary hypertension, in particular as mentioned hereafter.

The present invention also describes a method of treatment and/or prevention of a disease or a condition in which the peripheral NMDA receptors are involved, like pulmonary hypertension diseases and in particular pulmonary arterial hypertension, comprising the administration of a compound of formula (I) according to the invention.

Advantageously, the present invention describes a method of prevention of a disease or a condition in which the peripheral NMDA receptors are involved, like pulmonary hypertension diseases and in particular pulmonary arterial hypertension, comprising the administration of a compound of formula (I) according to the invention.

Indeed, compounds of formula (I) of the present invention are very useful as vascular protectors in prevention, for example in pre-operative or in the prevention of inflammation phenomena in extracorporeal circulation (ECC).

Within the meaning of the invention, the term "prevent" or "prevention" with respect to an event is intended to mean the decrease of a risk of occurrence of said event.

In the context of the present invention, the following abbreviations and empirical formulae are used:

ALI Acute Lung Injury
ARDS Acute Respiratory Distress Syndrome
BB Brain and Blood
BBB Blood-Brain Barrier CDCl$_3$ Deuterated chloroform
CNS Central Nervous System
CO Cardiac Output
DMSO Dimethyl Sulfoxide
IR InfraRed
hPASMC Human Pulmonary Arterial Smooth Muscle Cells
HRMS High Resolution Mass Spectroscopy
LiAlH$_4$ or LAH Lithium Aluminium Hydride
mPAP Mean Pulmonary Arterial Pressure
Na$_2$SO$_4$ Sodium Sulfate
NMDA N-Methyl-D-Aspartate
NMDAR N-Methyl-D-Aspartate Receptor
NMR Nuclear Magnetic Resonance
PAH Pulmonary Arterial Hypertension
PH Pulmonary Hypertension
RT-PCR Reverse Transcription Polymerase Chain Reaction
RVSP Right Ventricular Systolic Pressure
SmBm Smooth Muscle Basal Medium
SmGm2 Smooth Muscle Growth Medium-2
THF Tetrahydrofuran
TLC Thin Layer Chromatography
VWF Von Willebrand Factor Other features and advantages of the invention will emerge more clearly from the description and examples that follow.

Compounds of the Invention

As above-mentioned, the cationic compounds according to the invention correspond to general formula (I):

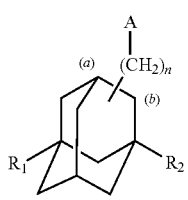

(I)

wherein:
R$_1$ and R$_2$ represent, independently of each other, a hydrogen atom or a (C$_1$-C$_6$)alkyl group;
the group —(CH$_2$)$_n$-A is linked to the cycle in position (a) or (b);
n is 0, 1, 2 or 3;
A represents a —NR$_3$R$_4$ group or a —N$^+$R$_3$R$_4$R$_5$ group;
R$_3$, R$_4$ and R$_5$ represent, independently of each other, a hydrogen atom, a (C$_1$-C$_{10}$)alkyl group, a (C$_1$-C$_{10}$) alkoxy group, a (C$_1$-C$_{10}$)alkyl-C(=NH)(—OH) group, a (C$_3$-C$_8$)cycloalkane group, a 6- to 10-membered aryl group or a 5- to 12-membered heteroaryl group; said alkyl or alkoxy groups being optionally substituted with one or more —NR$_6$R$_7$ group, —N$^+$R$_6$R$_7$R$_8$ group, (C$_3$-C$_8$)cycloalkane group, 6- to 10-membered aryl group or 5- to 12-membered heteroaryl group;
with R$_6$, R$_7$ and R$_8$ represent, independently of each other, a hydrogen atom or a (C$_1$-C$_6$)alkyl; and
the compound of formula (I) contains at least one positive charged nitrogen atom;
provided that R$_1$ and R$_2$ are not both a hydrogen atom; and
provided that when R$_1$ and R$_2$ are a methyl group, the group —(CH$_2$)$_n$-A is linked to the cycle in position (a), and n is 0, then A is not a group —N$^+$H$_3$.

The present invention also describes compounds corresponding to general formula (I):

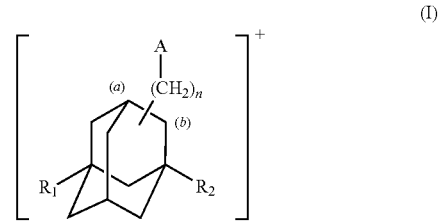

(I)

wherein:
R$_1$ and R$_2$ represent, independently of each other, a hydrogen atom or a (C$_1$-C$_6$)alkyl group;
the group —(CH$_2$)$_n$-A is linked to the cycle in position (a) or (b);
n is 0, 1, 2 or 3;
A represents a —NR$_3$R$_4$ group or a N$^+$R$_3$R$_4$R$_5$ group;
R$_3$, R$_4$ and R$_5$ represent, independently of each other, a hydrogen atom, a (C$_1$-C$_{10}$)alkyl group, a (C$_1$-C$_{10}$) alkoxy group, a (C$_1$-C$_{10}$)alkyl-C(=NH)(—OH) group, a (C$_3$-C$_8$)cycloalkane group, a 6- to 10-membered aryl group or a 5- to 12-membered heteroaryl group; said alkyl or alkoxy groups being optionally substituted with one or more —NR$_6$R$_7$ group, —N$^+$R$_6$R$_7$R$_8$ group, (C$_3$-C$_8$)cycloalkane group, 6- to 10-membered aryl group or 5- to 12-membered heteroaryl group;
with R$_6$, R$_7$ and R$_8$ represent, independently of each other, a hydrogen atom or a (C$_1$-C$_6$)alkyl; and
the positive charge of the compound being carried by at least a nitrogen atom.

As mentioned above, it is understood that when A represents a —N$^+$R$_3$R$_4$R$_5$ group, then R$_3$, R$_4$ and R$_5$ cannot represent a hydrogen atom, and when at least one of R$_3$, R$_4$ or R$_5$ represents an alkyl or alkoxy group substituted with at least one —N$^+$R$_6$R$_7$R$_8$ group, then R$_6$, R$_7$ and R$_8$ cannot represent a hydrogen atom.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

In the context of the present invention, the following definitions apply:
C$_t$-C$_z$: a carbon-based chain possibly containing from t to z carbon atoms in which t and z may take values from 1 to 10; for example, C$_1$-C$_6$ is a carbon-based chain possibly containing from 1 to 6 carbon atoms.
an alkyl: a linear or branched saturated aliphatic group, in particular comprising from 1 to 6 carbon atoms. Examples that may be mentioned include methyl, ethyl, n-propyl, isopropyl, n-butyl, isobutyl, tert-butyl, n-pentyl, etc. . . .
an alkoxy: a radical —O-alkyl in which the alkyl group is as defined previously.
a cycloalkane group: a non aromatic mono- or bicyclic saturated or partially saturated or unsaturated ring containing 3 to 8 carbon atoms, optionally substituted with one or more radicals chosen from (C$_1$-C$_6$)alkyl and/or 6- to 10-membered aryl. Examples of cycloalkane group that may be mentioned include cyclopropane, cyclobutane, cyclopentane, cyclopentene, cyclohexane or cyclohexene.

an aryl: a monocyclic or bicyclic aromatic group containing between 6 and 10 carbon atoms. By way of examples of an aryl group, mention may be made of phenyl or naphthyl group. Preferably, the aryl group is phenyl.

a heteroaryl: a 5- to 12-membered monocyclic or bicyclic aromatic group containing from 1 to 5 heteroatoms chosen from O, S and N. Examples of monocyclic heteroaryls that may be mentioned include imidazolyl, pyrazolyl, thiazolyl, oxazolyl, isothiazolyl, isoxazolyl, furyl, thienyl, oxadiazolyl, thiadiazolyl, triazolyl, tetrazolyl, pyridinyl, pyrazinyl, pyrimidinyl, pyridazinyl and triazinyl. Examples of bicyclic heteroaryls that may be mentioned include indolyl, isoindolyl, benzofuryl, benzothiophenyl, benzoxazolyl, benzimidazolyl, indazolyl, benzothienyl, isobenzofuryl, isobenzothiazolyl, pyrrolo[2,3-c]pyridyl, pyrrolo[2,3-b]pyridyl, pyrrolo[3,2-b]pyridyl, pyrrolo[3,2-c]pyridyl, pyrrolo[1,2-a]pyridyl, quinolyl, isoquinolyl, cinnolinyl, quinazolinyl, quinoxalinyl, pyrrolo[1,2-a]imidazolyl, imidazo[1,2-a]pyridyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridyl, imidazo[4,5-c]pyridyl, pyrazolo[2,3-a]pyridyl, pyrazolo[2,3-a]pyrimidinyl, pyrazolo[2,3-a]pyrazinyl, thiazolo[5,4-b]pyridyl, thiazolo[5,4-c]pyridyl, thiazolo[4,5-c]pyridyl, thiazolo[4,5-b]pyridyl, oxazolo[5,4-b]pyridyl, oxazolo[5,4-c]pyridyl, oxazolo[4,5-c]pyridyl, oxazolo[4,5-b]pyridyl, isothiazolo[5,4-b]pyridyl, isothiazolo[5,4-c]pyridyl, isothiazolo[4,5-c]pyridyl, isothiazolo[4,5-b]pyridyl, isoxazolo[5,4-b]pyridyl, isoxazolo[5,4-c]pyridyl, isoxazolo[4,5-c]pyridyl and isoxazolo[4,5-b]pyridyl. The heteroaryl groups may be more preferably chosen among quinolyl or pyridinyl groups.

According to one embodiment, $R_1$ and $R_2$ are chosen among a hydrogen atom or a methyl group, and preferably are both a methyl group.

According to a preferred embodiment, the group —$(CH_2)_n$-A is linked to the cycle in position (a).

In particular, n is 0 or 1, and preferably n is 0.

Among the compounds of general formula (I) used according to the invention, a subgroup of compounds is constituted by the compounds of formula (Ia):

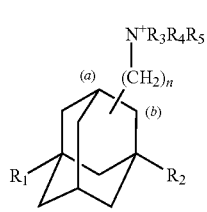

(Ia)

wherein $R_1$, $R_2$, $R_3$, $R_4$, $R_5$ and n are as defined above.

Preferably, $R_3$, $R_4$ and $R_5$ represent, independently of each other, a ($C_1$-$C_{10}$)alkyl group.

According to a particular embodiment, at least one of $R_3$, $R_4$ and $R_5$ represents a methyl group, and preferably at least two of $R_3$, $R_4$ and $R_5$ represent a methyl group.

Advantageously, $R_3$, $R_4$ and $R_5$ are simultaneously a methyl group.

According to another embodiment, $R_3$ and $R_4$ are a methyl group and $R_5$ represent a ($C_1$-$C_{10}$)alkyl group substituted with a ($C_3$-$C_8$)cycloalkane group.

It is clear that features of the above-mentioned embodiments may be combined with each other, unless specifically noted otherwise.

Among the compounds of general formula (I) or (Ia), mention may be made especially of the following compounds:

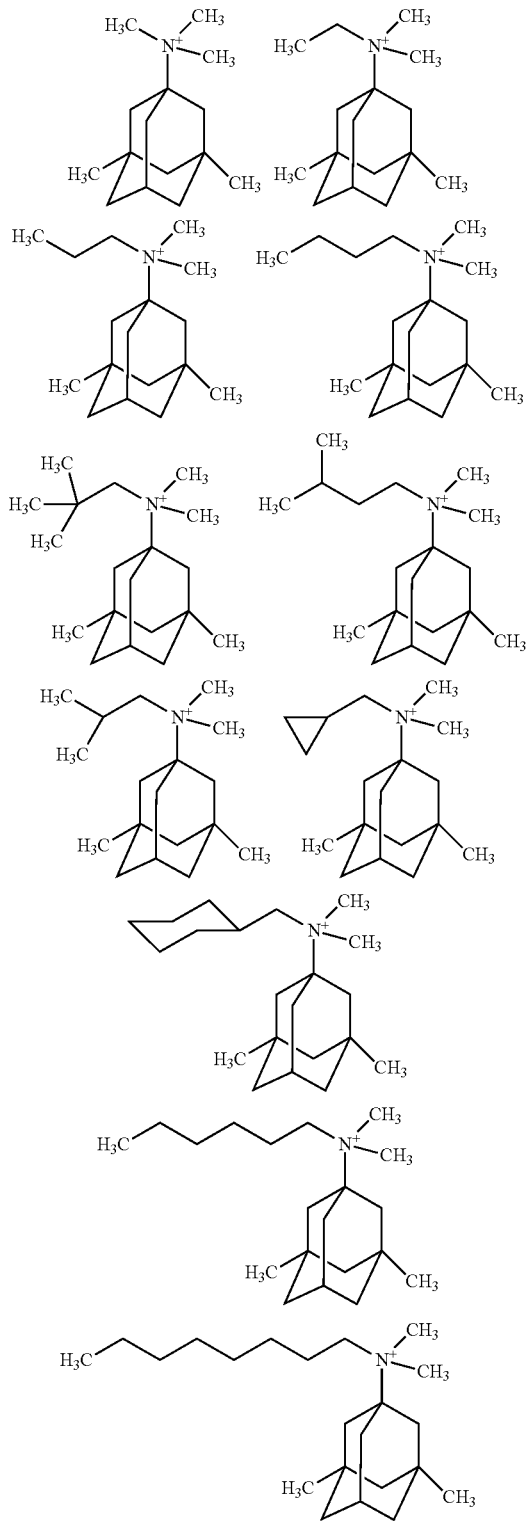

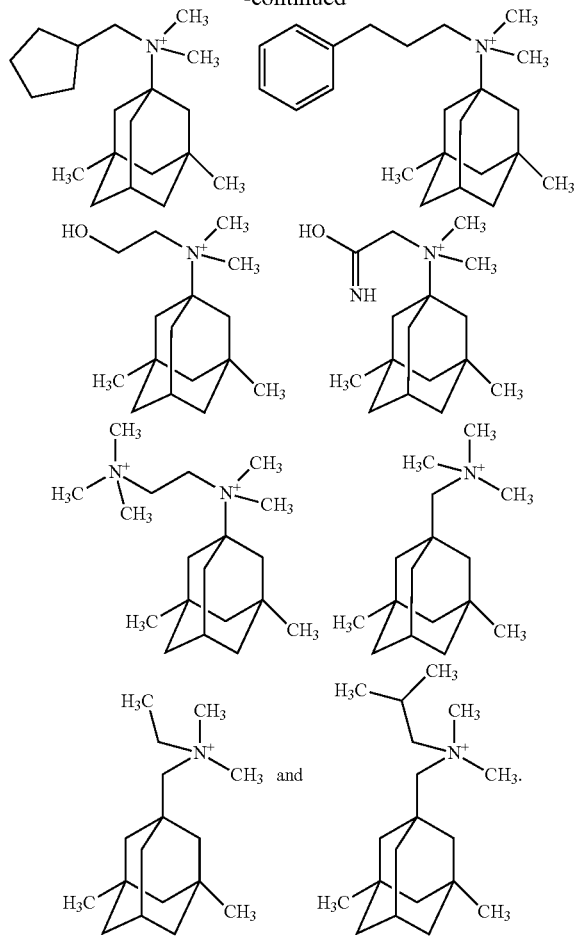
The present invention also describes the following compounds:
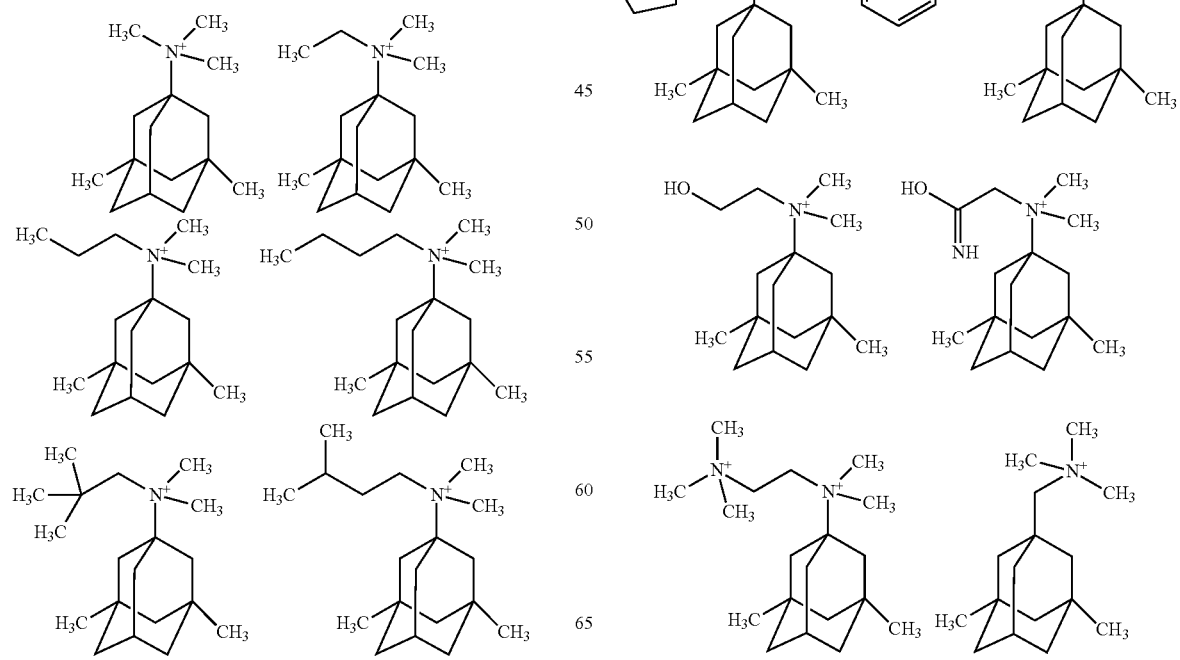
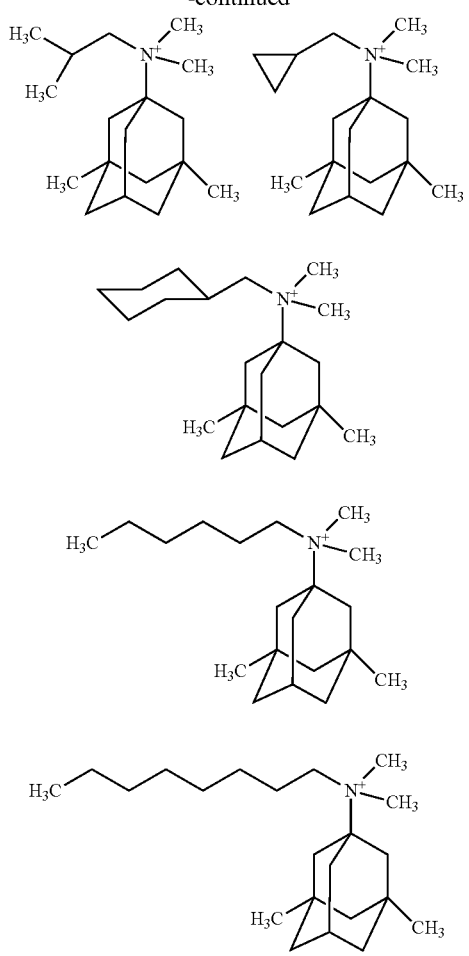

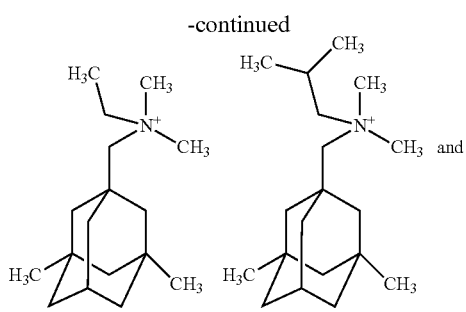

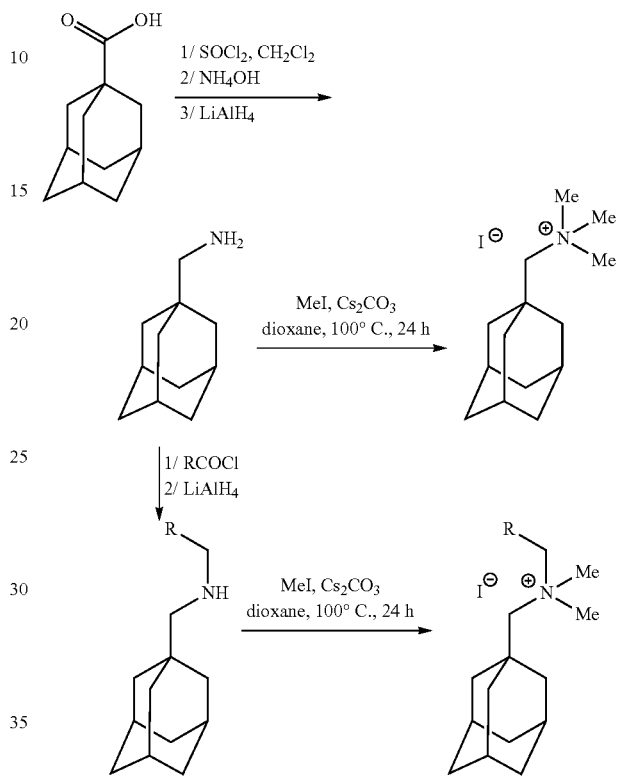

According to another embodiment, the synthesis of compounds of the present invention may be accomplished according to Scheme 2 below. For this synthesis, a similar sequence is used starting from 1-adamantanecarboxylic acid. To obtain other compounds of the present invention, similar sequences may be used starting from 1-aminoadamantane, or from 2-amino adamnatane.

Scheme 2

Preparation of the Compounds of the Invention

The compounds of the invention may be prepared according to methods well-known by the skilled artisan, as illustrated in the examples that follow.

According to a first embodiment, the synthesis of compounds of the present invention may be accomplished according to a three-step strategy starting from a bromoadamantane derivative, as illustrated in Scheme 1 below.

The sequence involves C—Br bond displacement with a primary amide reactant, reduction of the carbonyl function of the amide compound formed and then quaternarnization of the nitrogen atom.

Scheme 1

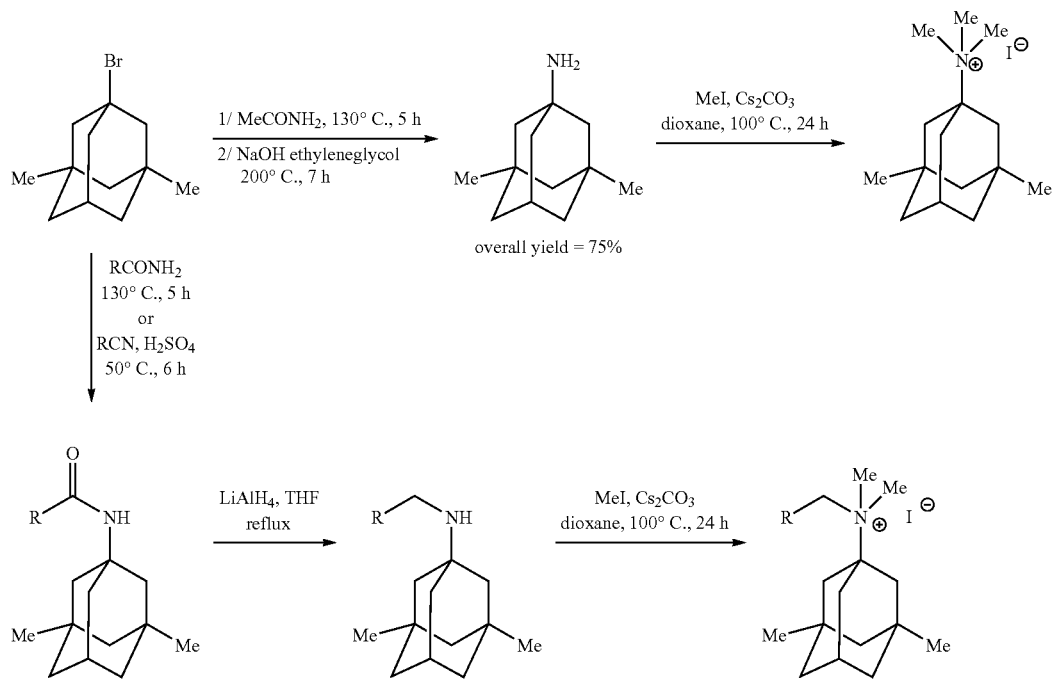

Applications

As specified previously and clearly illustrated by the following examples, the compounds according to the present invention are useful as peripheral NMDA receptor antagonists.

The present invention therefore describes a method for preventing and/or inhibiting and/or treating a disease or a condition in which the peripheral NMDA receptors are involved, comprising at least a step of administering to an individual in need thereof at least an effective amount of at least one compound in accordance with the invention.

In particular, the disease or the condition may be chosen among pulmonary hypertension, such as pulmonary arterial hypertension or thromboembolic pulmonary hypertension, pulmonary diseases involving inflammation, fibrosis and remodeling such as asthma, non-neuronal cancers such as colon, breast, lung or thyroid carcinoma, diabetes, atherosclerosis, sickle cell disease, diseases involving thrombosis, acute infections such as ARDS syndrome or ALI, chronic infectious diseases such as gastric ulcer induced by *Helicobacter pylori*, inflammatory/autoimmune diseases such as rheumatoid arthritis and irritable Bowel syndrome and osteoarthritis, heart failure, arrhythmias, renal disorders, pain, in particular peripheral neuropathic pain, psoriasis, atopic dermatitis and osteoporosis.

As mentioned above, pulmonary hypertension covers five groups of diseases.

The first group is pulmonary arterial hypertension. PAH may be associated with idiopathic and heritable PAH (bone morphogenetic protein receptor type 2 (BMPR2), ALK-1, Endoglin (ENG), SMAD9, Caveolin-1 (CAV1), KCNK3), with drug- and toxin-induced PAH, with connective tissue diseases, with human immunodeficiency virus, with portal hypertension, with congenital heart diseases, with schistosomiasis, with pulmonary veno-occlusive disease, pulmonary capillary hemangiomatosis, and persistent PH of the newborn.

The second group is PH due to left heart disease. It encompasses the most frequent form of PH, i.e. left ventricular systolic dysfunction, left ventricular diastolic dysfunction, valvular disease and congenital/acquired left heart inflow/outflow tract obstruction and congenital cardiomyopathies.

The third group is PH due to lung diseases and/or hypoxia. This group comprises patients with parenchymal lung diseases or other causes of hypoxia in whom the presence of PH is considered directly related to these underlying diseases. More particularly, it comprises chronic obstructive pulmonary disease, interstitial lung disease, other pulmonary diseases with mixed restrictive and obstructive pattern, sleep-disordered breathing, alveolar hypoventilation disorders, chronic exposure to high altitude and development lung diseases.

The fourth group is chronic thromboembolic pulmonary hypertension.

The fifth group is PH with unclear or multifactorial mechanisms. Included in this group are numerous forms of PH in which multiple pathophysiological mechanisms might be implicated in the elevation in pulmonary vascular pressures. It encompasses hematologic disorders (chronic haemolytic anemia, myelo-proliferative disorders, splenectomy), systemic disorders (sarcoidosis, pulmonary histiocytosis, lymphangioleiomyomatosis), metabolic disorders (glycogen storage disease, Gaucher disease, thyroid disorders) and others such as tumoral obstruction, fibrosing mediastinitis, chronic renal failure and segmental PH.

Of course, this recent classification is constantly evolving, and new groups and/or subgroups, also covered in the context of the present invention, are regularly discovered.

More specifically, according to the present invention, the disease or the condition is pulmonary hypertension, such as pulmonary arterial hypertension or thromboembolic pulmonary hypertension, and preferably pulmonary arterial hypertension.

The compounds according to the invention may be used for the preparation of medicaments.

Thus, according to yet another of its aspects, the present invention relates to a medicament comprising as pharmaceutical active agent at least one compound according to the invention.

According to another of its aspects, the present invention relates to a pharmaceutical composition comprising at least one compound according to the invention, and at least one pharmaceutically acceptable excipient.

According to one embodiment, a pharmaceutical composition of the invention may be intended to be administered separately, sequentially or simultaneously with an agent useful for the prevention and/or the inhibition and/or the treatment of a disease condition, said agent being different from the compound of formula (I) of the invention.

Thus, the present invention also relates to a pharmaceutical composition comprising at least one compound according to the invention in combination with at least one other therapeutic agent, and at least one pharmaceutically acceptable excipient.

According to one embodiment, the compounds of the present invention may be used alone or combined with one other therapeutic agent, for example vasodilator agents, other glutamate receptor antagonists (ionotropic and/or metabotropic), and in particular other NMDAR antagonists, chemotherapeutic agents, other pulmonary hypertension regimen or radiotherapeutic regimen and their mixtures.

Preferably, the present invention relates to a pharmaceutical composition comprising at least one compound according to the invention in combination with at least one other therapeutic agent, and preferably with vasodilator agents and/or other glutamate receptor antagonists (ionotropic and/or metabotropic), and in particular other NMDAR antagonists.

In the meaning of the present invention, "glutamate receptor antagonists" comprises two families: ionotropic (ion channels) and metabotropic (receptors with seven transmembrane domains). Among ionotropic, there are NMDAR, AMPA and Kainates. Ionotropic and metabotropic families are more particularly defined in the Guide to Pharmacology (IUPHAR/BP S).

Thus, according to one embodiment, a method of the invention may comprise the step of administering a compound of formula (I) in accordance with the invention, separately, sequentially or simultaneously with another therapeutic agent, and preferably with vasodilator agents and/or other glutamate receptor antagonists (ionotropic and/or metabotropic), and in particular NMDAR antagonists.

With respect to the use of the claimed compounds, in particular for treating pulmonary hypertension, it may be particularly advantageous to combine them with another or several others conventional therapeutic active(s) already considered in the treatment of such diseases. Since the claimed compounds acts according a specific new route, it may be expected to achieve a better result by simultaneously acting through different therapeutic routes.

In particular, this embodiment may allow reducing the therapeutic doses of respective compounds of the present invention, to administrate to the patient, thus allowing less adverse effects. In addition, this embodiment allows achieving additive or synergistic effect of the respective combined compounds of the present invention.

Thus, the present invention also describes a method of treatment of pulmonary hypertension, and in particular pulmonary arterial hypertension, comprising the administration of a claimed compound, advantageously combined with the administration of at least one active agent selected among the group consisting of vasodilator agents, other glutamate receptor antagonists (ionotropic and/or metabotropic), and in particular other NMDAR antagonists, chemotherapeutic agents, other pulmonary hypertension regimen or radiotherapeutic regimen and their mixtures.

For example, the compounds of the present invention may be used combined with endothelin receptor antagonists (ERAs), such as bosentan (Tracleer™, Actelion) and ambrisentan (Letairis™, Gilead), prostacyclin derivatives such as epoprostenol (Flolan™, Gsk, Actelion), treprostinil (Remodulin™, United Therapeutics) and Iloprost™ (Actelion), or PDE5 inhibitors such as Sildenafil (Revatio™, Pfizer) and Tadalafil (Adcirca™, Lilly).

As examples of chemotherapeutic agents that may be suitable for the invention, one may mention chemotherapeutic agents chosen from alkylating agents, intercalating agents, antimicrotubule agents, antimitotics, antimetabolites, antiproliferative agents, antibiotics, immunomodulatory agents, anti-inflammatories, kinases inhibitors, anti-angiogenic agents, antivascular agents, oestrogenic and androgenic hormones.

A radiotherapeutic regimen may be administrated by exposing an individual in need thereof to a source of ionizing radiation such as X-ray, gamma-ray or beta-ray.

The pharmaceutical compositions may contain more particularly an effective dose of at least one compound according to the invention.

An "effective dose" means an amount sufficient to induce a positive modification in the condition to be regulated or treated, but low enough to avoid serious side effects. An effective amount may vary with the pharmaceutical effect to obtain or with the particular condition being treated, the age and physical condition of the end user, the severity of the condition being treated/prevented, the duration of the treatment, the nature of other treatments, the specific compound or composition employed, the route of administration, and like factors.

A compound of formula (I) according to the invention may be administered in an effective dose by any of the accepted modes of administration in the art.

In one embodiment, a compound of the invention may be used in a composition intended to be administered by oral, nasal, sublingual, aural, ophthalmic, topical, rectal, vaginal, urethral, or parenteral injection route.

The route of administration and the galenic formulation will be adapted by one skilled in the art pursuant to the desired pharmaceutical effect.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

A medicament or pharmaceutical composition of the invention may be in the form of tablets, pills, powders, lozenges, sachets, cachets, elixirs, suspensions, emulsions, solutions, syrups, aerosols, sprays, ointments, gels, creams, sticks, lotions, pastes, soft and hard gelatine capsules, suppositories, sterile injectable solutions, sterile packages powders and the like.

The present invention will be better understood by referring to the following examples and figures which are provided for illustrative purpose only and should not be interpreted as limiting in any manner the instant invention.

FIGURES

FIG. 1: Effect of NMDAR knockout in PASMCs on hemodynamics and cardiac remodeling in pulmonary hypertension in the hypoxic mouse model of PH (NS means not significant, and results are expressed as mean±SEM).

Figure 2:
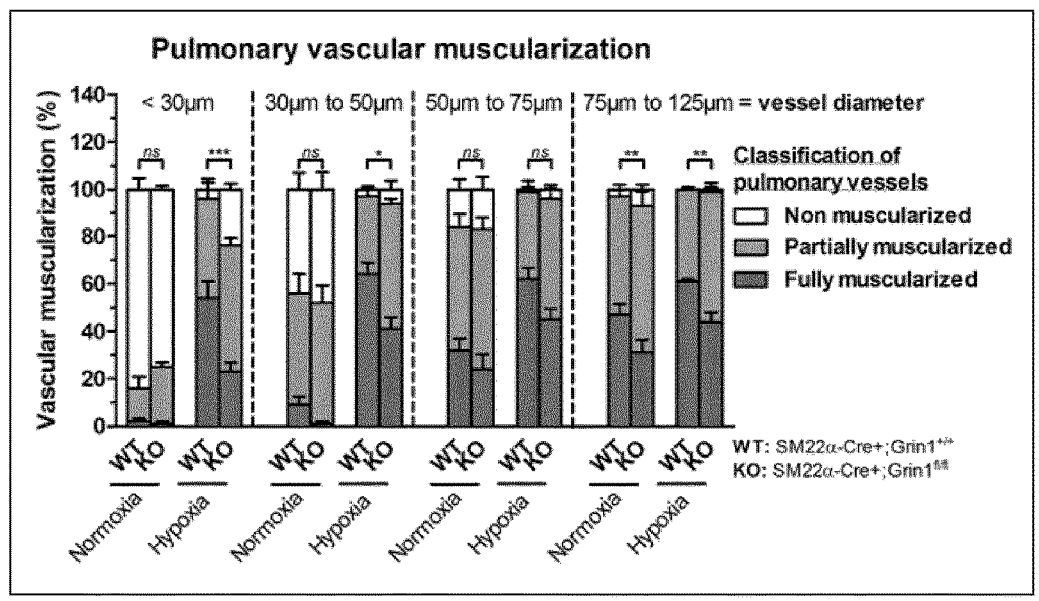

FIG. 2: Effect of NMDAR knockout in PASMCs on vascular remodeling in pulmonary hypertension in the hypoxic mouse model of PH (NS means not significant, and results are expressed as mean±SEM; Statistical significance is indicated; *$p<0.05$, $p<0.01$, *$p<0.001$).

EXAMPLES

Methods

Animal Models of Pulmonary Hypertension

All animals were used in strict accordance to the European Union regulations (Directive 2010/63/UE) for animal experiments. All animals were maintained in a temperature and humidity-controlled room with a 12 hours/12 hours light/dark cycle with access to a standard chow and water ad libitum.

Following procedures performed on mice, were approved by the ethical committee CEEA26 (Animal experimentation ethic committee N°26) and the French ministry of higher education and research.

Transgenic mice strains used are B6.12954-Grin1tm2Stl/J (further named as GRIN1fl/fl mice), B6.12956-Tagln tm2(cre)Yec/J (further named as Tagln-cre mice) (both from JACKSON LABORATORY) and B6.Cg-Tg(Tek-cre/ERT2)1Arnd/ArndCnrm (further named as Tek-cre mice) (EUROPEAN MOUSE MUTANT ARCHIVE).

Briefly, GRIN1fl/fl mice were crossed with either Tek-cre mice or tagln-cre mice. For NMDAR knocked out in smooth muscle cells, experiments were performed on male Tagln-cre×GRIN1fl/fl mice and male Tagln-cre mice were used as controls. For NMDAR knocked out in endothelial cells, experiments were performed on male Tek-cre×GRIN1fl/fl mice and male Tek-cre mice were used as controls after 5 weeks of Tamoxifen-containing chow (HARLAN LABORATORIES) administration followed by 1 week of standard chow. In both experiments, pulmonary hypertension was induced exposing mice to 3 weeks of hypoxia (10% $FiO_2$). Then, mice were submitted to anesthesia induced by inhalation of isoflurane 3% mixed with air and maintained decreasing isoflurane concentration between 1% and 1.5%. The heart was taken out the thoracic cage, auricles were removed and right ventricles were separated from left ventricles associated to septa. The weight of each part was measured and the ratio of the right ventricle weigh to the left ventricle with septum weigh was calculated for each mouse. Lungs were processed inflating them with 10 mL of a mixture of saline and OCT 1/1 ratio (Shandon™ Cryomatrix™, THERMOFISCHER SCIENTIFIC). Ventricles and inflated lungs were then frozen in cooled isopentane (VWR) and stored at −80° C.

Morphometric Analysis

6 μm thick sections of mouse lungs were cut with a cryomicrotome (LEICA MICROSYSTEMS). Sections were allowed to dry during 1 hour under a hood. Then, they were fixed in cold acetone for 10 minutes. 10% goat serum plus 5% mouse serum were incubated for 1 hour to prevent unspecific binding of antibodies. Anti-VWF and Anti-alpha smooth muscle cell-FITC antibodies were incubated in presence of 2% mouse serum during 1 hour at room temperature. A negative control was performed omitting primary antibodies. The secondary antibody was incubated during 30 minutes in presence of 2% mouse serum. DAPI (LIFE TECHNOLOGIES) diluted at 1/500 was incubated during 1 minute. Glass slides were finally mounted using Dako Fluorescent mounting medium (DAKO). Sections were then analyzed using Eclipse 80i microscope coupled to Nis Elements BR2.30 software (NIKON).

For morphometric analysis performed on mouse lungs, intrapulmonary arterioles were divided in four groups based on their external diameter: less than 30 μm, from 30 μm to 50 μm, from 50 μm to 75 μm and from 75 μm to 125 μm. 20 arterioles per category identified with the VWF staining were qualified as non muscularized, partially muscularized or fully muscularized based on the alpha smooth muscle actin staining. 5 mice/group were included in the study.

In Vivo Brain Penetration Measurement: Drug Administration and Sampling of Brain and Plasma The femoral vein of male Sprague-Dawley rats (CRL) weighing around 250 g was surgically catheterized at least 72 hours prior to the experiment. The drug was administered as 3.75 h constant-rate intravenous infusion to approach steady state, using a flow rate of 0.8 mL/h, corresponding to dosage of 4 mg/kg (1.067 mg/kg/h, i.e. 1 mg/rat of ~250 g). The vehicle used was saline.

At the end of the infusion, the rats were anesthetized by inhalation of isoflurane, and blood was collected in a heparinized tube from the abdominal aorta, followed by immediate rinsing of the bloodstream for 2 minutes with saline at a rate of 15 mL/min using a peristaltic pump and left intraventricle cannula (flowing via right atrium). The brain (without cerebellum) was removed, and transferred in a tube and homogenized in two volumes of deionized water using a tissue homogenizer (Precellys24). All samples were stored at −20° C. until analysis. Plasma and brain homogenate sample preparation was performed using solid phase extraction on OASIS® WCX (Waters) and compounds were quantified by reversed phase liquid chromatography and positive electrospray ionization and multiple reaction monitoring mass spectrometry (LC-MS/MS).

Cultures of Hippocampal Neurons

For hippocampal neurons isolation and culture, all animals were used in strict accordance to the European Union regulations (Directive 2010/63/UE) for animal experiments. 18 day-pregnant female Wistar rats were decapitated, and fetuses were rapidly extracted from uterus and transferred in dissection solution (50 ml PBS (LIFE TECHNOLOGIES)+ 50 units/ml penicillin-streptomycin (Abx) (THERMOFISCHER SCIENTIFIC)+0.6% glucose. The rat fetus brains were quickly removed and placed in dissection solution before hippocampus extraction. Hippocampus were collected in HBSS (43.5 ml PBS, 0.6% glucose, 100 mM HEPES (LIFE TECHNOLOGIES), 100 units/ml Abx) and digested by addition of 0.25% trypsin (LIFE TECHNOLOGIES) and 0.1% DNAse I. After 10 minutes incubation at 37° C., 10% FBS (THERMOFISCHER SCIENTIFIC) was added to stop digestion. Cells were then mechanically dissociated by gentle pipetting to obtain uniform suspension. After centrifugation (10 minutes, 100 G) supernatant was removed and cell pellet was suspended in HC medium (50 ml neurobasal medium, 1 ml B27 supplement, 500 μl glutamine 200 mM 100× (all from LIFE TECHNOLOGIES), 50 units/ml Abx) plus 10% FBS and without Abx. Cells were counted and 630,000 cells were dispatched in each poly-D-lysine-coated 35 mm petri dishes (BD Falcon, CORNING) containing 2 ml HC for culture. After 6 days of culture, cytosine (3-D-arabinofuranoside (Ara-C) was added to inhibit proliferation of glial cells. Cells were then used from DIV 14. Cells were cultured at 37° C. in a humidified atmosphere of 5% $CO_2$ and 95% air.

Electrophysiology

Chemicals used for patch-clamp solutions were provided by Sigma-Aldrich. TTX was provided by R&D, CNQX by Abcam. Whole-cell voltage clamp recordings from rat hippocampal neurons were made with patch pipettes (5-6 MΩ) filled with intracellular solution (in mM): 150 CsCl, 5 EGTA, 10 HEPES; its pH was adjusted to 7.2 with NaOH. The external bath solution contained (in mM): 140 NaCl, 3 KCl, 2 $CaCl_2$, 10 HEPES, 10 glucose, 0.5 μM TTX, 20 μM picrotoxin and 20 μM CNQX; its pH was adjusted to 7.4 with CsOH. The membrane potential was clamped at −60 mV. Currents were monitored using an AxoPatch200B patch clamp amplifier (Axon Instruments, Sunnyvale, Calif., USA) filtered at 2 kHz and digitized at 100 Hz. Experiments were controlled by data acquisition board (National Instruments). Data were analyzed by Exel and GraphPad software. Liquid junction potentials were measured with the patch clamp amplifier. Transmembrane currents were evoked in acutely isolated neurons by the application of 100 μM NMDA and 20 μM D-serine. Antagonists of NMDA receptors were applied at increasing concentration. Cells were constantly perfused using gravity-fed bath at 1-2 ml/min. To calculate the percentage block by antagonist, residual desensitization of NMDA-induced currents was compensated by fitting exponentials to the pre-antagonist portion of traces.

Statistical Analysis

Results are expressed as mean+SEM of measurement unless otherwise indicated. Gaussian distribution of all data was assessed using Kolmogorov-Smirnov test or Shapiro-Wilk depending on sample size. To compare two groups of data, either unpaired t test or Mann-Whitney test were used depending on the data distribution. For multiple comparisons, one-way analysis of variance followed by Bonferroni test or Kruskal-Wallis followed by Dunn's tests were used when it was appropriate. Results from transgenic mice were analyzed with a two-way analysis of variance followed by a Bonferroni test. Differences were considered significant with a P value<0.05. Statistical analysis was performed with Prism 6 (GRAPHPAD SOFTWARE) and Excel softwares.

Example 1

Preparation of the Compounds According to the Invention

In accordance with the invention, the preparation of compounds of general formula (I) is illustrated below.

General Procedure A for the Preparation of 3,5-dimethyladamantan-1-amide

200 μL of 1-bromo-3,5-dimethyladamantane (1 mmol) and 10 equivalent of the corresponding amide were mixed neat in a microwave type tube. The vial is sealed. The mixture was heated at the fusion point of the amide, and stirred at this temperature during 10 to 20 hours. After cooling at room temperature, 100 mL of dichloromethane was added to the reaction mixture. The solution obtained was washed successfully with 25 mL of water, and 25 mL of brine. Organic layers were dried over sodium sulfate, concentrated under reduce pressure, at 10 mbar, and the crude product was purified by column chromatography on silica gel.

General Procedure B for the Preparation of 3,5-dimethyladamantan-1-amide

400 μL of 1-bromo-3,5-dimethyladamantane (2 mmol) and 5 equivalent of the appropriate nitrile were mixed neat in a microwave type tube. After addition of 200 μL of sulfuric acid 96% (4 mmol), the vial is sealed and the mixture was heated at 50° C. under agitation during 6 hours. After cooling at room temperature, 40 mL of ice water was added to the reaction mixture, and the aqueous phase was extracted with 100 mL of dichloromethane. Organic layers were washed with 20 mL of a saturated solution of sodium bicarbonate then with 20 mL of water. After drying over $Na_2SO_4$ and evaporation of the solvent under reduce pressure, at 10 mbar, the crude product was purified by column chromatography on silica gel.

General Procedure C for Reduction of 3,5-dimethyladamantan-1-amide

To 1 equivalent of a solution of adamantanamide derivative in 0.2 M of anhydrous THF was added 5 equivalent of $LiAlH_4$ under nitrogen atmosphere at 0° C. After stirring at room temperature for an additional period of 30 minutes, the mixture was heated at reflux for 5 to 18 hours (reaction monitored by TLC). After being allowed to cool to room temperature, the mixture was treated with drop-to-drop addition of water till complete destruction of excess LAH. The mixture was then filtered on celite pad, washed with diethyl ether and the resultant solution was washed with brine. After drying with $Na_2SO_4$, evaporation of the solvent under reduced pressure, at 10 mbar, the amine was directly engaged in the next step without purification.

General Procedure D for Permethylation of 3,5-dimethyladamantan-1-amine

To a solution of 1 mmol of the corresponding amine in 3 mL of dioxane in a microwave-type tube, were added 1.3 g of cesium carbonate (4 mmol) and 5 mL of methyl iodide (80 mmol). The vial is sealed, and the mixture was heated at 100° C. under stirring for 24 hours. After being allowed to cool to room temperature, the precipitate formed was filtered on sintered filter and washed successively with 100 mL of ethyl acetate, then 50 mL of dichloromethane. The organic layers were concentrated under reduced pressure, at 10 mbar, to give the desired quaternarized ammonium iodide salt.

N,N,N,3,5-Pentamethyladamantan-1-ammonium iodide (Compound N°1)

Compound N°1 is prepared according to the general procedure D.
To a solution of 108 mg of 3,5-dimethyladamantan-1-amine hydrochloride (0.5 mmol) in 2 mL of dioxane were added 648 mg of cesium carbonate (2 mmol) and 2.5 mL of methyl iodide (40.2 mmol) to give 122 mg of Compound N°1 as a white solid without purification.
Yield: 70%.
Melting point=290-293° C.
$^1$H NMR δ (300 MHz, $CDCl_3$) (ppm): 3.3 (s, 9H), 2.43 (m, 1H), 1.93 (br s, 2H), 1.67 (dd, J=20.8 Hz, 10.9 Hz, 4H), 1.45-1.31 (m, 4H), 1.28-1.14 (m, 2H), 0.99 (s, 6H).
$^{13}$C NMR δ (75 MHz, $CDCl_3$) (ppm): 74.9, 49.4, 49.1, 41.5, 41.2, 41.4, 34.1, 34.0, 30.6, 30.1.
IR (neat) ($cm^{-1}$): $\lambda_{max}$=3452, 2954, 2924, 2902, 2849, 1489, 1457, 1415, 1365, 1341, 1181, 987, 904, 841, 827, 717, 642.
HRMS (ESI positive): Calculated for $C_{15}H_{28}N$ $[M-I]^+$ 222.2222; Found 222.2213.

N-Ethyl-N,N-3,5-tetramethyladamantan-1-ammonium iodide (Compound N°2)

Compound N°2 is prepared according to the general procedure D.
To a solution of 245 mg of N-Ethyl-3,5-dimethyladamantan-1-amine (1.2 mmol) in 2 mL of dioxane were added 1.53 g of cesium carbonate (4.7 mmol) and 6 mL of methyl iodide (96.4 mmol) to give 317 mg of Compound N°2 as a white solid without purification.
Yield=73%.
Melting point=248-250° C.
$^1$H NMR δ (300 MHz, $CDCl_3$) (ppm): 3.52 (q, J=7.2 Hz, 2H), 3.1 (s, 6H), 2.48 (m, 1H), 2.03 (br s, 2H), 1.75 (dd, J=22.5 Hz, 10.8 Hz, 4H), 1.56 (t, J=7.2 Hz, 3H), 1.50-1.36 (m, 4H), 1.32-1.20 (m, 2H), 1.24 (br s, 2H), 1.22 (s, 3H), 1.19 (s, 3H), 1.02 (s, 6H).
$^{13}$C NMR δ (75 MHz; $CDCl_3$) (ppm): 54.2, 49.5, 44.8, 41.5, 41.4, 34.3, 34.2, 30.8, 30.1, 9.9.
IR (neat) ($cm^{-1}$): $\lambda_{max}$=3420, 2949, 2903, 2864, 2847, 1485, 1454, 1366, 1349, 1266, 1015, 987, 815, 905.
HRMS (ESI positive): Calculated for $C_{16}H_{30}N$ $[M-I]^+$ 236.2378; Found 236.2384.

N-Propyl-N,N-3,5-tetramethyladamantan-1-ammonium iodide (Compound N°3)

Compound N°3 is prepared according to the general procedure D.
To a solution of 221 mg of N-propyl-3,5-dimethyladamantan-1-amine (1 mmol) in 2 mL of dioxane were added 1.3 g of cesium carbonate (4 mmol) and 5 mL of methyl iodide (80 mmol) to give 264 mg of Compound N°3 as a white solid without purification.
Yield=70%.
Melting point=204-206° C.
$^1$H NMR δ (300 MHz, $CDCl_3$) (ppm): 3.29-3.20 (m, 2H), 3.1 (s, 6H), 2.46 (m, 1H), 2.00 (br s, 2H), 1.99-1.89 (m, 2H), 1.72 (dd, J=22.6 Hz, 11.0 Hz, 4H), 1.59-1.52 (m, 4H), 1.48-1.34 (m, 4H), 1.31-1.18 (m, 2H), 1.1 (t, J=7.2 Hz, 3H), 1.01 (s, 6H). $^{13}$C NMR δ (75 MHz; $CDCl_3$) (ppm): 63.4, 62.4, 35.6, 33.3, 22.4, 19.0, 18.2, 12.2.
IR (neat) ($cm^{-1}$): $\lambda_{max}$=3452, 2962, 2946, 2909, 2898, 2864, 2844, 1481, 1454, 1416, 1365, 1342, 1263, 1181, 920, 813, 787, 761, 725, 641.
HRMS (ESI positive): Calculated for $C_{17}H_{32}N$ $[M-I]^+$ 250.2535; Found 250.2532.

N-Butyl-N,N-3,5-tetramethyladamantan-1-ammonium iodide (Compound N°4)

Compound N°4 is prepared according to the general procedure D.

To a solution of 235 mg of N-propyl-3,5-dimethyladamantan-1-amine (1 mmol) in 2 mL of dioxane were added 1.3 g of cesium carbonate (4 mmol) and 5 mL of methyl iodide (80 mmol) to give 282 mg of Compound N°4 as a white solid without purification.

Yield=72%.

Melting point=200-204° C.

$^1$H NMR δ (300 MHz, CDCl$_3$) (ppm): 3.32-3.24 (m, 2H), 3.1 (s, 6H), 2.46 (m, 1H), 2.00 (br s, 2H), 1.91-1.79 (m, 2H), 1.72 (dd, J=22.2 Hz, 11.1 Hz, 4H), 1.55-1.44 (m, 4H), 1.44-1.37 (m, 4H), 1.31-1.18 (m, 2H), 1.03 (t, J=7.3 Hz, 3H), 1.00 (s, 6H).

$^{13}$C NMR δ (75 MHz; CDCl$_3$) (ppm): 62.5, 62.4, 35.6, 33.3, 23.5, 22.4, 19.0, 18.2, 13.8.

IR (neat) (cm$^{-1}$): λ$_{max}$=3457, 2951, 2903, 2866, 2845, 1479, 1455, 1414, 1364, 1342, 1261, 1180, 920, 899, 839, 784, 724, 640.

HRMS (ESI positive): Calculated for C$_{18}$H$_{34}$N [M-I]$^+$ 264.2691; Found 264.2687.

N,N-3,5-Tetramethyl-N-neopentyladamantan-1-ammonium iodide (Compound N°5)

Compound N°5 is prepared according to the general procedure D.

To a solution of 67 mg of N-neopenthyl-3,5-dimethyladamantan-1-amine (0.25 mmol) in 1 mL of dioxane were added 330 mg of cesium carbonate (1 mmol) and 1.2 mL of methyl iodide (19.3 mmol) to give 20 mg of Compound N°5 as a pale yellow solid without purification.

Yield: 20%.

Melting point=198-200° C.

$^1$H NMR δ (300 MHz, CDCl$_3$) (ppm): 3.21 (s, 6H), 3.15 (s, 2H), 2.47 (m, 1H), 2.03 (br s, 2H), 1.73 (dd, J=24.7 Hz, 11.0 Hz, 4H), 1.41 (dd, J=26.8 Hz, 12.9 Hz, 4H), 1.31 (s, 9H), 1.24 (br s, 2H), 1.02 (s, 6H).

$^{13}$C NMR δ (75 MHz; CDCl$_3$) (ppm): 80.5, 67.9, 49.6, 46.5, 41.5, 40.9, 34.6, 33.7, 31.2, 30.1.

IR (neat) (cm$^{-1}$): λ$_{max}$=3400, 2952, 2921, 2903, 2867, 2848, 1486, 1455, 1414, 1375, 1363, 1262, 956, 919, 807, 776, 726, 641.

HRMS (ESI positive): Calculated for C$_{19}$H$_{36}$N [M-I]$^+$ 278.2848; Found 278.2843.

N-isoPentyl-N,N-3-5-tetramethyladamantan-1-ammonium iodide (Compound N°6

Compound N°6 is prepared according to the general procedure D.

To a solution of 135 mg of N-isopentyl-3,5-dimethyladamantan-1-amine (0.54 mmol) in 1.5 mL of dioxane were added 700 mg of cesium carbonate (2.16 mmol) and 2.7 mL of methyl iodide (43.4 mmol) to give 140 mg of Compound N°6 as a white solid without purification.

Yield: 60%.

Melting point=77-79° C.

$^1$H NMR δ (300 MHz, CDCl$_3$) (ppm): 3.28-3.20 (m, 2H), 3.10 (s, 6H), 2.46 (m, 1H), 2.01 (br s, 2H), 1.81-1.64 (m, 7H), 1.41 (dd, J=20.3 Hz, 12.5 Hz, 4H), 1.27-1.22 (m, 2H), 1.02 (d, J=4.1 Hz, 6H), 1.01 (s, 6H).

$^{13}$C NMR δ (75 MHz, CDCl$_3$) (ppm): 77.8, 57.6, 49.5, 45.5, 41.5, 41.4, 34.4, 34.2, 32.0, 30.8, 30.1, 26.7, 22.8.

IR (neat) (cm$^{-1}$): λ$_{max}$=3420, 3024, 2951, 2904, 2866, 2846, 1477, 1454, 1416, 1367, 817.

HRMS (ESI positive): Calculated for C$_{19}$H$_{36}$N [M-I]$^+$ 278.2848; Found 278.2849.

N-isoButyl-N,N-3,5-tetramethyladamantan-1-ammonium iodide (Compound N°7

Compound N°7 is prepared according to the general procedure D.

To a solution of 40 mg of N-isobutyl-3,5-dimethyladamantan-1-amine (0.17 mmol) in 1 mL of dioxane were added 200 mg of cesium carbonate (6.2 mmol) and 850 µL of methyl iodide (13.7 mmol) to react during 3 hours to give 30 mg of Compound N°7 as a yellow solid without purification.

Yield: 45%.

Melting point=197-200° C.

$^1$H NMR δ (300 MHz, CDCl$_3$) (ppm): 3.15 (s, 6H), 3.08 (d, J=4.9 Hz, 2H), 2.46 (m, 2H), 2.00 (br s, 2H), 1.72 (dd, J=23.8 Hz, 11.4 Hz, 4H), 1.41 (dd, J=26.4 Hz, 13.6 Hz), 1.24 (br s, 2H), 1.22 (s, 3H), 1.19 (s, 3H), 1.01 (s, 6H).

$^{13}$C NMR δ (75 MHz, CDCl$_3$) (ppm): 78.5, 66.1, 49.6, 45.7, 41.6, 41.3, 34.5, 34.1, 31.0, 30.1, 24.4, 24.2.

IR (neat) (cm$^{-1}$): λ$_{max}$=3420, 2951, 2922, 2903, 2847, 1482, 1456, 1414, 1364, 1342, 1261, 1093, 1014, 919, 806, 776, 722, 640.

HRMS (ESI positive): Calculated for C$_{18}$H$_{34}$N [M-I]$^+$ 264.2691; Found 264.2688.

N-(Cyclopropylmethyl)-N,N-3,5-tetramethyladamantan-1-ammonium iodide (Compound N°8)

Compound N°8 is prepared according to the general procedure D.

To a solution of 100 mg of N-(cyclopropylmethyl)-3,5-dimethyladamantan-1-amine (0.43 mmol) in 2 mL of dioxane were added 553 mg of cesium carbonate (1.7 mmol) and 2.1 mL of methyl iodide (33.7 mmol) to give 113 mg of Compound N°8 as a yellow solid by precipitation with pentane of ethyl acetate filtrate, without purification.

Yield: 77%.

Melting point=180-183° C.

$^1$H NMR δ (300 MHz, CDCl$_3$) (ppm): 3.29 (d, J=6.9 Hz, 2H), 3.15 (s, 6H), 2.41 (m, 1H), 1.98 (d, J=2.8 Hz, 2H), 1.76 (m, 1H), 1.71 (dd, J=20.7 Hz, 10.8 Hz, 4H), 1.37 (dd, J=33.4 Hz, 13.1 Hz, 4H), 1.21 (br s, 2H), 0.96 (s, 6H), 0.9-0.82 (m, 2H), 0.67-0.59 (m, 2H).

$^{13}$C NMR δ (75 MHz, CDCl$_3$) (ppm): 76.9, 63.2, 49.4, 45.6, 41.5, 41.2, 34.3, 34.1, 30.7, 30.0, 5.8, 5.4.

IR (neat) (cm$^{-1}$): λ$_{max}$=3464, 2948, 2922, 2903, 2864, 2845, 1614, 1478, 1456, 1413, 1365, 1343, 1264, 1180, 1033, 970, 811, 768, 731.

HRMS (ESI positive): Calculated for C$_{18}$H$_{32}$N [M-I]$^+$ 262.2535; Found 262.2529.

N-(Cyclohexylmethyl)-N,N-3,5-tetramethyladamantan-1-ammonium iodide (Compound N°9)

Compound N°9 is prepared according to the general procedure D.

To a solution of 100 mg of N-(cyclohexylmethyl)-3,5-dimethyladamantan-1-amine (0.36 mmol) in 2 mL of dioxane were added 470 mg of cesium carbonate (1.45 mmol) and 1.8 mL of methyl iodide (28.9 mmol) to give 124 mg of Compound N°9 as a white solid, without purification.

Yield: 80%.

Melting point=247-249° C.

$^1$H NMR δ (300 MHz, CDCl$_3$) (ppm): 3.14 (s, 6H), 2.99 (d, J=4.4 Hz, 2H), 2.45 (m, 1H), 2.10 (m, 1H), 1.99 (br s, 2H), 1.89 (d, J=11.7 Hz, 2H), 1.89-1.63 (m, 7H), 1.40 (dd, J=27 Hz, 13.1 Hz, 6H), 1.28-1.11 (m, 5H), 1.00 (s, 6H).

$^{13}$C NMR δ (75 MHz, CDCl$_3$) (ppm): 78.3, 65.2, 49.5, 45.6, 41.5, 41.2, 34.5, 34.0, 33.0, 30.9, 30.1, 26.1, 25.5.

IR (neat) (cm$^{-1}$): λ$_{max}$=3029, 2950, 2921, 2907, 2849, 1478, 1453, 1417, 1264, 951, 933, 905, 818, 786.

HRMS (ESI positive): Calculated for C$_{21}$H$_{38}$N [M-I]+ 304.3004; Found 304.2998.

N-nHexyl-N,N-3,5-tetramethyladamantan-1-ammonium iodide (Compound N°10)

Compound N°10 is prepared according to the general procedure D.

To a solution of 100 mg of N-nhexyl-3,5-dimethyladamantan-1-amine (0.38 mmol) in 2 mL of dioxane were added 490 mg of cesium carbonate (1.5 mmol) and 1.9 mL of methyl iodide (30.5 mmol) to give 130 mg of Compound N°10 as a yellow solid, without purification.

Yield: 82%.

Melting point=192-195° C.

$^1$H NMR δ (300 MHz, CDCl$_3$) (ppm): 3.28-3.20 (m, 2H), 3.10 (s, 6H), 2.46 (m, 1H), 2.00 (br s, 2H), 1.91-1.80 (m, 2H), 1.72 (dd, J=22.7 Hz, 10.5 Hz, 4H), 1.48-1.32 (m, 10H), 1.26-1.22 (m, 2H), 1.0 (s, 6H), 0.9 (t, J=7.1 Hz, 3H).

$^{13}$C NMR δ (75 MHz, CDCl$_3$) (ppm): 58.5, 49.4, 45.5, 41.5, 41.2, 34.3, 34.1, 31.4, 30.7, 30.0, 26.5, 23.7, 22.5.

IR (neat) (cm$^{-1}$): λ$_{max}$=3452, 3023, 2951, 2922, 2902, 2865, 2846, 1479, 1455, 1415, 1365, 1343, 1311, 1180, 968, 900, 839, 816, 730.

HRMS (ESI positive): Calculated for C$_{20}$H$_{38}$N [M-I]$^+$ 292.3004; Found 292.3005.

N-nOctyl-N,N-3,5-tetramethyladamantan-1-ammonium iodide (Compound N°11)

Compound N°11 is prepared according to the general procedure D.

To a solution of 100 mg of N-nOctyl-3,5-dimethyladamantan-1-amine (0.34 mmol) in 2 mL of dioxane were added 445 mg of cesium carbonate (1.37 mmol) and 1.7 mL of methyl iodide (27.3 mmol) to give 132 mg of Compound N°11 as a white solid, without purification.

Yield: 87%.

Melting point=173-175° C.

$^1$H NMR δ (300 MHz, CDCl$_3$) (ppm): 3.28-3.19 (m, 2H), 3.10 (s, 6H), 2.46 (m, 1H), 2.00 (br s, 2H), 1.91-1.80 (m, 2H), 1.72 (dd, J=22.7 Hz, 10.5 Hz, 4H), 1.48-1.16 (m, 18H), 1.0 (s, 6H), 0.88 (t, J=6.7 Hz, 3H).

$^{13}$C NMR δ (75 MHz, CDCl$_3$) (ppm): 58.4, 49.4, 45.5, 41.4, 41.2, 34.3, 34.0, 31.7, 30.7, 30.0, 29.3, 29.1, 26.8, 23.8, 22.6, 14.1.

IR (neat) (cm$^{-1}$): λ$_{max}$=3464, 2952, 2923, 2901, 2848, 1480, 1455, 1414, 1365, 1342, 1311, 1264, 1180, 990, 920, 900, 839, 814, 725, 617.

N-(Cyclopentylmethyl)-N,N-3,5-tetramethyladamantan-1-ammonium iodide (Compound N°12)

Compound N° 12 is prepared according to the general procedure D.

To a solution of 100 mg of N-(Cyclohexylmethyl)-3,5-dimethyladamantan-1-amine (0.38 mmol) in 2 mL of dioxane were added 490 mg of cesium carbonate (1.51 mmol) and 1.9 mL of methyl iodide (30.5 mmol) to give 24 mg of Compound N°12 as a white solid, without purification.

Yield: 15%.

Melting point=213-215° C.

$^1$H NMR δ (300 MHz, CDCl$_3$) (ppm): 3.27 (d, J=5.9 Hz, 2H), 3.13 (s, 6H) 2.45 (m, 1H), 2.17-2.05 (m, 2H), 2.00 (br s, 2H), 1.99 (br s, 2H), 1.80-1.62 (m, 8H), 1.49-1.27 (m, 5H), 1.24 (br s, 2H), 1.00 (s, 6H).

$^{13}$C NMR δ (75 MHz, CDCl$_3$) (ppm): 64.2, 49.5, 46.0, 41.5, 41.3, 35.5, 34.4, 34.1, 33.9, 30.9, 30.1, 25.2.

IR (neat) (cm$^{-1}$): λ$_{max}$=3441, 2949, 2904, 2865, 2845, 1477, 1454, 1414, 1365, 1344, 1263, 1180, 920, 900, 813, 785, 728, 640.

HRMS (ESI positive): Calculated for C$_{20}$H$_{36}$N [M-I]$^+$ 290.2848; Found 290.2848.

N-(3-Phenylpropyl)-N,N-3,5-tetramethyladamantan-1-ammonium iodide (Compound N°13)

Compound N°13 is prepared according to the general procedure D.

To a solution of 150 mg of N-(3-Phenylpropyl)-3,5-dimethyladamantan-1-amine (0.5 mmol) in 2 mL of dioxane were added 650 mg of cesium carbonate (2 mmol) and 2.5 mL of methyl iodide (40.2 mmol) to give 95 mg of Compound N°13 as a white solid, without purification.

Yield: 42%.

Melting point=180-182° C.

$^1$H NMR δ (300 MHz, CDCl$_3$) (ppm): 7.33-7.27 (m, 4H), 7.25-7.18 (m, 1H), 3.44-3.35 (m, 2H), 3.04 (s, 6H), 2.81 (t, J=7.4 Hz, 2H), 2.41 (m, 1H), 2.27-2.14 (m, 2H), 1.93 (b s, 2H), 1.65 (dd, J=22.9 Hz, 11.0 Hz, 4H), 1.43-1.29 (m, 4H), 1.27-1.13 (m, 2H), 0.97 (s, 6H).

$^{13}$C NMR δ (75 MHz, CDCl$_3$) (ppm): 140.0, 128.8, 128.7, 126.6, 57.7, 49.3, 45.4, 41.4, 41.2, 34.2, 34.0, 32.4, 30.7, 30.0, 25.7.

IR (neat) (cm$^{-1}$): λ$_{max}$=2955, 2904, 2842, 1477, 1454, 1366, 1341, 1260, 1181, 906, 833, 813, 781, 732, 716, 701, 638.

HRMS (ESI positive): Calculated for C$_{23}$H$_{36}$N [M-I]$^+$ 326.2848; Found 326.2846.

N-(2-Hydroxethyl)-N,N-3,5-tetramethyladamantan-1-ammonium iodide (Compound N°14)

Compound N° 14 is prepared according to the general procedure D.

To a solution of 150 mg of 2-(3,5-Dimethyladamantan-1-yl)amino)ethan-1-ol (0.67 mmol) in 3 mL of dioxane were added 870 mg of cesium carbonate (2.7 mmol) and 3.3 mL of methyl iodide (53 mmol) to give 191 mg of Compound N°14 as a white solid, without purification.

Yield: 75%.

Melting point=220-223° C.

$^1$H NMR δ (300 MHz, CDCl$_3$) (ppm): 4.23 (br s, OH), 4.25 (br s, 2H), 3.63-3.56 (m, 2H), 3.19 (s, 6H), 2.44 (m, 1H), 1.95 (br s, 2H), 1.76-1.62 (m, 4H), 1.46-1.32 (m, 4H), 1.29-1.16 (m, 2H), 0.99 (s, 6H).

$^{13}$C NMR δ (75 MHz, CDCl$_3$) (ppm): 59.5, 56.3, 49.4, 45.9, 43.2, 41.5, 40.9, 34.2, 33.8, 30.7, 30.0.

IR (neat) (cm$^{-1}$): λ$_{max}$=3376, 2951, 2904, 2847, 1629, 1456, 1414, 1364, 1342, 1260, 1180, 1090, 1046, 918, 901, 811, 769, 727, 643.

HRMS (ESI positive): Calculated for C$_{16}$H$_{30}$NO [M-I]$^+$ 252.2327; Found 252.2326.

N-(2-Hydroxy-2-iminoethyl)-N,N-3,5-tetramethyladamantan-1-ammonium iodide (Compound N°15)

Compound N°15 is prepared according to the general procedure D.

To a solution of 50 mg of 2-(-3,5-Dimethyladamantan-1-yl-amino)-acetimidic acid (0.21 mmol) in 1 mL of dioxane were added 272 mg of cesium carbonate (0.84 mmol) and 1.1 mL of methyl iodide (17.7 mmol) to react during 14 hours to give 35 mg of Compound N°15 as a white solid, without purification.

Yield: 42%.

Melting point=216-219° C.

$^1$H NMR δ (300 MHz, CDCl$_3$) (ppm): 8.88 (br s, OH), 5.86 (br s, NH), 4.42 (s, 2H), 3.22 (s, 6H), 2.50 (m, 1H), 2.08 (br s, 2H), 1.82 (dd, J=24.0 Hz, 10.6 Hz, 4H), 1.43 (dd, J=27.2 Hz, 12.9 Hz, 4H), 1.27 (br s, 2H), 1.03 (s, 6H).

$^{13}$C NMR δ (75 MHz, CDCl$_3$) (ppm): 165.7, 80.6, 58.5, 49.4, 45.1, 41.4, 41.3, 34.8, 34.1, 31.1, 30.1.

IR (neat) (cm$^{-1}$): λ$_{max}$=3331, 3238, 3156, 2950, 2907, 2845, 1693, 1607, 1446, 1418, 1360, 1311, 1261, 785, 697.

HRMS (ESI positive): Calculated for C$_{16}$H$_{29}$N$_2$O [M-I]$^+$ 265.2280; Found 265.2274.

N1-(3,5-Dimethyladamantan-1-yl)-N1,N1,N2,N2, N2-pentamethylethane-1,2-diammonium iodide (Compound N°16)

Compound N°16 is prepared according to the general procedure D.

To a solution of 100 mg of N-ethanol-memantine (0.45 mmol) in 2 mL of dioxane were added 600 mg of cesium carbonate (1.85 mmol) and 2.3 mL of methyl iodide (37 mmol). The crude solid obtained is purified over preparative plates to deliver 55 mg of Compound N°16 as an orange amorphous solid.

Yield: 22%.

$^1$H NMR δ (300 MHz, DMSO-d6) (ppm): 3.95 (m, 2H), 3.57 (m, 2H), 3.20 (s, 9H), 2.92 (s, 6H), 2.32 (m, 1H), 1.95 (br s, 2H), 1.80-1.68 (m, 4H), 1.46-1.36 (m, 2H), 1.33-1.15 (m, 4H), 0.94 (s, 6H).

$^{13}$C NMR δ (75 MHz, DMSO-d6) (ppm): 78.9, 57.9, 53.3, 50.1, 48.5, 47.8, 33.8, 32.3, 30.4, 29.7.

IR (neat) (cm$^{-1}$): λ$_{max}$=3440, 3009, 2950, 2921, 2904, 2865, 2846, 1486, 1455, 1416, 1364, 1343, 1311, 1180, 963, 953, 920, 785, 748.

3,5-dimethyladaman-1-yl-N,N,N-trimethylmethanamonium iodide (Compound N°17)

Compound N°17 is prepared according to the general procedure D.

To a solution of 60 mg of 3,5-dimethyladamantan-1-yl-methanamine (0.3 mmol) in 2 mL of dioxane were added 400 mg of cesium carbonate (12 mmol) and 1.5 mL of methyl iodide (24 mmol) to give 80 mg of Compound N°17 as a white solid without purification.

Yield: 71%.

Melting point=288-292° C.

$^1$H NMR δ (300 MHz, CDCl$_3$) (ppm): 3.6 (s, 9H), 3.44 (s, 2H), 2.15 (br s, 1H), 1.69 (br s, 2H), 1.42 (dd, J=25.2 Hz, 11.5 Hz, 4H), 1.38-1.33 (m, 4H), 1.24-1.10 (m, 2H), 0.85 (s, 6H).

$^{13}$C NMR δ (75 MHz, CDCl$_3$) (ppm): 77.7, 56.7, 50.4, 48.0, 42.4, 40.5, 38.0, 31.3, 30.5, 29.2.

IR (neat) (cm$^{-1}$): λ$_{max}$=3442, 2997, 2946, 2895, 2842, 1491, 1453, 1420, 1376, 1360, 1344, 1265, 972, 943, 925, 895, 874, 734, 701.

HRMS (ESI positive): Calculated for C$_{16}$H$_{30}$N [M-I]$^+$ 236.2378; Found 236.2381.

N-3,5-dimethyladaman-1-yl-methyl-N,N-trimethyl-ethananamonium iodide (Compound N°18)

Compound N°18 is prepared according to the general procedure D.

To a solution of 110 mg of 3,5-dimethyladamantan-1-yl-methanamine (0.5 mmol) in 2 mL of dioxane were added 675 mg of cesium carbonate (2.1 mmol) and 2.5 mL of methyl iodide (40 mmol) to give 130 mg of Compound N°18 as a white solid without purification.

Yield: 69%.

Melting point=261° C.

$^1$H NMR δ (300 MHz, CDCl$_3$) (ppm): 3.82 (q, J=7.2 Hz, 2H), 3.44 (s, 6H), 3.35 (s, 2H), 2.16 (br s, 1H), 1.70 (br s, 2H), 1.24-1.10 (m, 11H), 1.38-1.33 (m, 2H), 0.85 (s, 6H).

$^{13}$C NMR δ (75 MHz; CDCl$_3$) (ppm): 74.7, 63.0, 53.3, 50.4, 48.2, 42.4, 40.6, 38.0, 31.4, 30.5, 29.3, 9.4.

IR (neat) (cm$^{-1}$): λ$_{max}$=3442, 2946, 2919, 2898, 2863, 2842, 1487, 1455, 1420, 1376, 1360, 1267, 1020, 972, 893, 732, 699.

HRMS (ESI positive): Calculated for C$_{17}$H$_{32}$N [M-I]$^+$ 250.2535; Found 250.2533.

N-3,5-dimethyladaman-1-yl-methyl-N,N, 2-trimethylpropan-1-anamonium iodide (Compound N°19)

Compound N°19 is prepared according to the general procedure D.

To a solution of 75 mg of N-3,5-dimethyladamantan-1-yl-methyl-2-methylpropan-1-amine (0.3 mmol) in 1 mL of dioxane were added 390 mg of cesium carbonate (1.2 mmol) and 1.5 mL of methyl iodide (24 mmol) to give 130 mg of Compound N°19 as a white solid without purification.

Yield: 84%.

Melting point=165-168° C.

$^1$H NMR δ (300 MHz, CDCl$_3$) (ppm): 3.59 (d, J=5.3 Hz, 2H), 3.48 (s, 6H), 3.42 (s, 2H), 2.31 (m, 1H), 2.15 (m, 1H), 1.70 (br s, 2H), 1.43 (dd, J=27 Hz, 11.1 Hz, 4H), 1.36 (br s, 4H), 1.19 (d, J=6.5 Hz, 6H), 1.19-1.10 (m, 2H), 0.85 (s, 6H).

$^{13}$C NMR δ (75 MHz, CDCl$_3$) (ppm): 76.1, 75.4, 53.8, 50.3, 48.4, 42.4, 40.7, 38.1, 31.3, 30.5, 29.3, 24.5, 23.4.

IR (neat) (cm$^{-1}$): λ$_{max}$=3400, 2945, 2894, 2863, 2838, 1487, 1454, 1373, 1361, 1344, 1262, 994, 969, 888, 876, 843, 737.

HRMS (ESI positive): Calculated for C$_{19}$H$_{36}$N [M-I]$^+$ 278.2848; Found 278.2848.

N,N,N-Trimethyladamantan-1-ammonium iodide (Compound N°20, not According to the Invention)

Compound N°20 is prepared according to the general procedure D.

To a solution of 188 mg of adamantan-1-amine hydrochloride (1 mmol) in 3 mL of dioxane were added 1.3 g of cesium carbonate (4 mmol) and 5 mL of methyl iodide (80 mmol) to give 240 mg of Compound N°20 as a white solid without purification.

Yield: 75%.

Melting point=325° C.

$^1$H NMR δ (300 MHz, CDCl$_3$) (ppm): 3.32 (s, 9H), 2.41 (br s, 3H), 2.06 (br d, J=2.6 Hz, 6H), 1.72 (dd, J=24.4 Hz, 13.1 Hz, 6H).

$^{13}$C NMR δ (75 MHz, CDCl$_3$) (ppm): 73.3, 48.9, 35.2, 35.1, 30.2.

IR (neat) (cm$^{-1}$): λ$_{max}$=3442, 2955, 2909, 2854, 1491, 1477, 1448, 1416, 1370, 1347, 1265, 1039, 957, 939, 800, 733, 701.

HRMS (ESI positive): Calculated for $C_{13}H_{24}N$ [M-I]$^+$ 194.1909; Found 194.1905.

Compound N°21, not According to the Invention

Compound N°21 is prepared according to the general procedure D.

To a solution of 94 mg of Adamantan-2-amine hydrochloride (0.5 mmol) in 2 mL of dioxane were added 0.81 g of cesium carbonate (2.5 mmol) and 2.5 mL of methyl iodide (40.2 mmol) to give 105 mg of Compound N°21 as a white solid, without purification.

Yield: 66%.

Melting point=344-346° C.

$^1$H NMR δ (300 MHz, CDCl$_3$) (ppm): 4.0 (br s, 1H), 3.52 (s, 9H), 2.64 (br s, 2H), 2.17-1.94 (m, 8H), 1.89-1.75 (m, 4H).

$^{13}$C NMR δ(75 MHz, CDCl$_3$) (ppm): 79.7, 54.3, 39.7, 37.3, 31.5, 29.0, 27.0, 26.0.

IR (neat) (cm$^{-1}$): λ$_{max}$=3400, 2998, 2924, 2907, 2862, 2849, 1491, 1476, 1420, 1352, 1274, 1099, 1039, 969, 941, 865, 819.

HRMS (ESI positive): Calculated for $C_{13}H_{24}N$ [M-I]$^+$ 194.1909; Found 194.1910.

Compound N°22, not According to the Invention

Compound N°22 is prepared according to the general procedure D.

To a solution of 90 mg of N-ethyladamantan-2-amine (0.5 mmol) in 2 mL of dioxane were added 0.81 g of cesium carbonate (2.5 mmol) and 2.5 mL of methyl iodide (40.2 mmol) to give 117 mg of Compound N°22 as a white solid, without purification.

Yield: 70%.

Melting point=300° C.

$^1$H NMR δ (300 MHz, CDCl$_3$) (ppm): 3.86 (q, J=7.3 Hz, 2H), 3.76 (br s, 1H), 3.40 (s, 6H), 2.61 (br s, 2H), 2.13-1.96 (m, 8H), 1.91-1.74 (m, 4H), 1.43 (t, J=7.3 Hz, 3H).

$^{13}$C NMR δ (75 MHz, CDCl$_3$) (ppm): 77.2, 60.7, 54.5, 51.3, 40.1, 37.6, 32.2, 28.9, 27.3, 26.0, 9.5.

IR (neat) (cm$^{-1}$): λ$_{max}$=3400, 3006, 2923, 2908, 2862, 2851, 1493, 1460, 1354, 1270, 1099, 1039, 967, 944, 864, 811.

HRMS (ESI positive): Calculated for $C_{16}H_{26}N$ [M-I]$^+$ 208.2065; Found 208.2059.

N-isoButyl-N,N-dimethyladamantan-2-ammonium iodide (Compound N°23, not According to the Invention)

Compound N°20 is prepared according to the general procedure D.

To a solution of 85 mg of N-isoButyladamantan-2-amine (0.41 mmol) in 2 mL of dioxane were added 0.53 g of cesium carbonate (1.64 mmol) and 1 mL of methyl iodide (16 mmol) to give 64 mg of Compound N°23 as a white solid, without purification.

Yield: 40%.

Melting point=227-229° C.

$^1$H NMR δ (300 MHz, CDCl$_3$) (ppm): 3.90 (br s, 1H), 3.58 (d, J=5.1 Hz, 2H), 3.43 (br s, 6H), 2.61 (br s, 2H), 2.33-2.22 (m, 1H), 2.13-1.96 (m, 8H), 1.90-1.75 (m, 4H), 1.21 (d, J=6.7 Hz, 6H).

$^{13}$C NMR δ (75 MHz, CDCl$_3$) (ppm): 78.1, 72.6, 60.7, 54.6, 51.9, 40.1, 37.6, 32.2, 29.0, 27.3, 26.1, 24.3, 23.6.

IR (neat) (cm$^{-1}$): λ$_{max}$=3464, 2966, 2919, 2854, 1491, 1469, 1372, 1271, 1099, 1039, 968, 916, 641.

HRMS (ESI positive): Calculated for $C_{16}H_{30}N$ [M-I]$^+$ 236.2378; Found 236.2372.

The table 1 below illustrates Compounds N°1 to N°19 of the invention:

TABLE 1 (I)

| No | Formula | R$_1$ | R$_2$ | (a) or (b) | n | A | R$_3$ | R$_4$ | R$_5$ | Counterion |
|---|---|---|---|---|---|---|---|---|---|---|
| 1 | (structure) | —CH$_3$ | —CH$_3$ | (a) | 0 | —N$^+$R$_3$R$_4$R$_5$ | —CH$_3$ | —CH$_3$ | —CH$_3$ | I$^-$ |
| 1' | (structure) | —CH$_3$ | —CH$_3$ | (a) | 0 | —N$^+$R$_3$R$_4$R$_5$ | —CH$_3$ | —CH$_3$ | —CH$_3$ | Cl$^-$ |

TABLE 1-continued (I)

[Structure: adamantane core with substituents R₁, R₂ at bridgehead positions and (CH₂)ₙ–A group at position (a) or (b)]

| No | Formula | R₁ | R₂ | (a) or (b) | n | A | R₃ | R₄ | R₅ | Counterion |
|----|---------|-----|-----|-----|---|---|-----|-----|-----|------|
| 2 | [ethyl dimethyl ammonium dimethyladamantane] | —CH₃ | —CH₃ | (a) | 0 | —N⁺R₃R₄R₅ | —CH₃ | —CH₃ | —CH₂—CH₃ | I⁻ |
| 3 | [propyl dimethyl ammonium dimethyladamantane] | —CH₃ | —CH₃ | (a) | 0 | —N⁺R₃R₄R₅ | —CH₃ | —CH₃ | —CH₂—CH₂—CH₃ | I⁻ |
| 4 | [butyl dimethyl ammonium dimethyladamantane] | —CH₃ | —CH₃ | (a) | 0 | —N⁺R₃R₄R₅ | —CH₃ | —CH₃ | —CH₂—CH₂—CH₂—CH₃ | I⁻ |
| 5 | [neopentyl dimethyl ammonium dimethyladamantane] | —CH₃ | —CH₃ | (a) | 0 | —N⁺R₃R₄R₅ | —CH₃ | —CH₃ | —CH₂—C(CH₃)₃ | I⁻ |
| 6 | [isopentyl dimethyl ammonium dimethyladamantane] | —CH₃ | —CH₃ | (a) | 0 | —N⁺R₃R₄R₅ | —CH₃ | —CH₃ | —CH₂—CH₂—CH(CH₃)₂ | I⁻ |

TABLE 1-continued
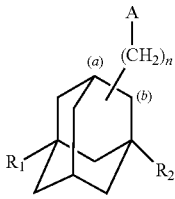
(I)
| No | Formula | $R_1$ | $R_2$ | (a) or (b) | n | A | $R_3$ | $R_4$ | $R_5$ | Counterion |
|----|---------|-------|-------|-----------|---|---|-------|-------|-------|------------|
| 7 | 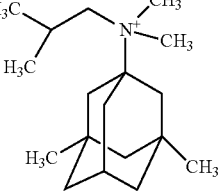 | —$CH_3$ | —$CH_3$ | (a) | 0 | —$N^+R_3R_4R_5$ | —$CH_3$ | —$CH_3$ | —$CH_2$—$CH(CH_3)_2$ | $I^-$ |
| 8 |  | —$CH_3$ | —$CH_3$ | (a) | 0 | —$N^+R_3R_4R_5$ | —$CH_3$ | —$CH_3$ | —$CH_2$—$(C_3H_5)$ | $I^-$ |
| 9 | 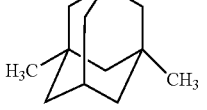 | —$CH_3$ | —$CH_3$ | (a) | 0 | —$N^+R_3R_4R_5$ | —$CH_3$ | —$CH_3$ | —$CH_2$—$(C_6H_{11})$ | $I^-$ |
| 10 |  | —$CH_3$ | —$CH_3$ | (a) | 0 | —$N^+R_3R_4R_5$ | —$CH_3$ | —$CH_3$ | —$(CH_2)_5$—$CH_3$ | $I^-$ |
| 11 | 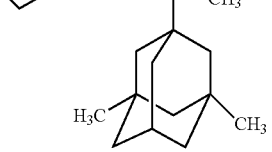 | —$CH_3$ | —$CH_3$ | (a) | 0 | —$N^+R_3R_4R_5$ | —$CH_3$ | —$CH_3$ | —$(CH_2)_7$—$CH_3$ | $I^-$ |
| 12 | 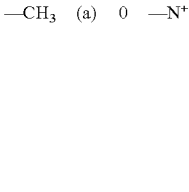 | —$CH_3$ | —$CH_3$ | (a) | 0 | —$N^+R_3R_4R_5$ | —$CH_3$ | —$CH_3$ | —$CH_2$—$(C_5H_9)$ | $I^-$ |

TABLE 1-continued (I)

| No | Formula | R₁ | R₂ | (a) or (b) | n | A | R₃ | R₄ | R₅ | Counterion |
|----|---------|-----|-----|-----------|---|---|-----|-----|-----|-----------|
| 13 | | —CH₃ | —CH₃ | (a) | 0 | —N⁺R₃R₄R₅ | —CH₃ | —CH₃ | —(CH₂)₃—(C₆H₅) | I⁻ |
| 14 | | —CH₃ | —CH₃ | (a) | 0 | —N⁺R₃R₄R₅ | —CH₃ | —CH₃ | —CH₂—CH₂—OH | I⁻ |
| 15 | | —CH₃ | —CH₃ | (a) | 0 | —N⁺R₃R₄R₅ | —CH₃ | —CH₃ | —CH₂—C(NH)(OH) | I⁻ |
| 16 | | —CH₃ | —CH₃ | (a) | 0 | —N⁺R₃R₄R₅ | —CH₃ | —CH₃ | —CH₂—CH₂—N⁺(CH₃)₃ | I⁻ |
| 17 | | —CH₃ | —CH₃ | (a) | 1 | —N⁺R₃R₄R₅ | —CH₃ | —CH₃ | —CH₂—N⁺(CH₃)₃ | I⁻ |

TABLE 1-continued

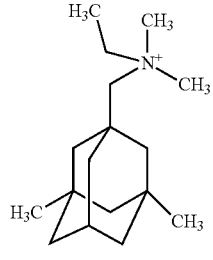

| No | Formula | R₁ | R₂ | (a) or (b) | n | A | R₃ | R₄ | R₅ | Counterion |
|---|---|---|---|---|---|---|---|---|---|---|
| 18 | 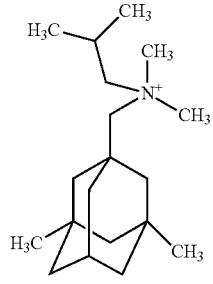 | —CH₃ | —CH₃ | (a) | 1 | —N⁺R₃R₄R₅ | —CH₃ | —CH₃ | —CH₂—N⁺(CH₃)₂(CH₂CH₃) | I⁻ |
| 19 | | —CH₃ | —CH₃ | (a) | 1 | —N⁺R₃R₄R₅ | —CH₃ | —CH₃ | —CH₂—CH(CH₃)₂ | I⁻ |

The compounds according to the invention were the subject of pharmacological assays.

Example 2

Role of NMDA Receptors in the Development of Pulmonary Hypertension

To understand the functional importance of NMDARs in smooth muscle cells, the Grin1 gene (encoding the obligatory GluN1 subunit) has been deleted from the smooth muscle cells of mice. These knock out mice for NMDAR in PASMC were produced breeding mice expressing Cre recombinase in smooth muscle cells with floxed GRIN1 mice (GRIN1: gene coding for GluN1 ubiquitous subunit of NMDARs).

Under chronic hypoxia (FiO₂ 10%, 3 weeks), KO mice develop an attenuated form of PH compared to control mice, with a decreased right ventricular pressure and cardiac hypertrophy (Fulton index) (FIG. 1). In FIG. 1, P<0.01 and p<0.001 in KO mice compared to wild type under hypoxia, for right ventricular systolic pressure and Fulton index, respectively.

After chronic hypoxia (FiO₂ 10%, 3 weeks), KO mice also have a decreased muscularization of small vessels (diameter <50 μm) compared to control mice (FIG. 2). Moreover, KO mice present less muscularized large vessels (75 μm<diameter <125 μm) in both normoxic and hypoxic conditions compared to control mice (FIG. 2).

These results indicate that knocking out NMDAR in PASMC attenuates pulmonary vascular cell remodeling, cardiac remodeling and PH in hypoxic mice. Thus, PASMC NMDA receptors contribute to pulmonary vascular cell remodeling, cardiac remodeling and to pulmonary hypertension.

Example 3

In Vivo Brain Penetration Measurements

Compounds of the present invention provide a mean to prevent Blood-Brain Barrier. This assumption has been verified on rats.

Among methods addressing central nervous system penetration in drug discovery, in vivo equilibrium distribution between blood and brain in rodents is the most commonly used parameter to evaluate brain penetration.

This parameter is defined as the ratio of concentrations in brain and blood, $Kp_{\text{"brain"}}$ ($C_{brain}/C_{plasma}$) or log(BB). Log (BB) is the logarithm of the ratio of the steady-state total concentration of a compound in the brain to that in the blood/plasma, $\log(BB)=\log(C_{brain}/C_{plasma})$. This parameter depends upon the passive diffusion characteristics, the implication of membrane transporters at the BBB level and the relative drug binding affinity differences between the plasma proteins and brain tissue. Generally, compounds with a brain/plasma ratio of greater than 0.3-0.5 are considered to have sufficient access to the CNS, compounds with a value greater than 1 freely cross the BBB, whereas compounds with a brain/plasma ratio smaller than 0.1 may be unable to enter the CNS.

Thus, the brain penetration of memantine and Compound N°1 was measured in rat by establishing the brain/plasma ratio, Kp"$_{brain}$" in triplicate (3 rats/Compound). The three tables below (Tables 1-3) show the results on plasma concentration, brain concentration and calculation of the Kp"$_{brain}$" for the two compounds memantine and Compound N° 1.

TABLE 1

Plasma concentration

| Compounds | Rat | Plasma concentration (ng/mL) | Mean | CV % |
|---|---|---|---|---|
| Memantine | 1 | 123.23 | 102.25 | 18.0 |
|  | 2 | 88.69 |  |  |
|  | 3 | 94.85 |  |  |
| Compound No1 | 4 | 34.77 | 27.47 | 23.2 |
|  | 5 | 23.11 |  |  |
|  | 6 | 24.52 |  |  |

Plasma concentration was measured in 3 rats for each compound memantine and Compound N°1. Compound N°1 still retains a good plasma concentration as compared to memantine.

TABLE 2

Brain concentration

| Compounds | Rat | Brain concentration (ng/g) | Mean | CV % |
|---|---|---|---|---|
| Memantine | 1 | 3342 | 3185 | 5.9 |
|  | 2 | 2977 |  |  |
|  | 3 | 3237 |  |  |
| Compound No1 | 4 | 3.03 | 2.5 | 56.5 |
|  | 5 | 0.90 |  |  |
|  | 6 | 3.57 |  |  |

Brain concentration was measured in 3 rats for each compound memantine and Compound N°1. Compound N°1 presents a very low brain concentration as compared to memantine.

TABLE 3

Calculation of Kp"$_{brain}$"

| Compounds | Rat | Kp"$_{brain}$" | Mean |
|---|---|---|---|
| Memantine | 1 | 27.12 | 31.6 |
|  | 2 | 33.57 |  |
|  | 3 | 34.13 |  |
| Compound No1 | 4 | 0.09 | 0.091 |
|  | 5 | 0.04 |  |
|  | 6 | 0.15 |  |

The Kp"$_{brain}$" value (defined as the total brain/plasma concentration ratio at steady state) was calculated in 3 rats for each compound memantine and Compound N°1. Compound N°1 presents a very low Kp"$_{brain}$" value (below 0.1) as compared to memantine.

In conclusion, as known and previously described, memantine penetrates freely across the BBB and intensively penetrate the CNS in rat. As we expected, due to the presence of a quaternary ammonium and as demonstrated by the Kp"$_{brain}$" value found below 0.1, the Compound N°1 does not penetrate the CNS in rat.

Example 4

In Vitro Activity

Previous studies have shown that the NMDAR exists in the peripheral vasculature.

All NMDAR subunits were examined by RT-PCR and sequencing in the peripheral endothelium and peripheral vascular smooth muscle cells. The sequences of these NMDAR subunits in both vascular cells showed a high similarity if not identity to the sequences of brain NMDAR (Chen H et al, *J Vasc Surg* 2005, Qureshi I et al *Vasc Med* 2005).

Thus, to provide the accuracy of a well-known and admitted screening system, the molecule described herein where tested in serial concentrations ranging from 1 nM to 100 µM for their NMDAR blocking activity using patch-clamp. Whole-cell voltage clamp recordings from rat hippocampal neurons were then used to calculate $IC_{50}$ for each molecule. The $IC_{50}$ is the concentration of an inhibitor where the response (or binding) is reduced by half.

TABLE 4

NMDAR antagonist activity of selected compounds

| Compound | $IC_{50}$ (µM) |
|---|---|
| Memantine | 1.0 |
| Compound No1 | 9.9 |
| Compound No1' | 11.6 |
| Compound No2 | 18.0 |
| Compound No3 | 29.0 |
| Compound No4 | 110 |
| Compound No6 | 14.3 |
| Compound No8 | 3.5 |
| Compound No9 | 35.2 |

Using this test the parent molecule memantine had an $IC_{50}$ of 1 µM, which is 5 consistent with its known antagonist activity (Traynelis S F et al *Pharmacological reviews* 2010). Compounds of the present invention have an activity ranging from 3.5 to 110 µM (Table 4). Notably, Compounds N°1 and N°1' have an activity in the 10 µM range in iodure or chlorure form. Of interest, results obtained with Compound N°8 ($IC_{50}$=3.5 µM) clearly demonstrate that structural modification on the nitrogen atom of memantine is not deleterious for activity.

The invention claimed is:
1. Cationic compound of formula (I):

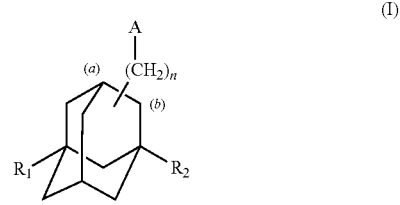

wherein:
$R_1$ and $R_2$ represent, independently of each other, a hydrogen atom or a ($C_1$-$C_6$)alkyl group;
the group —$(CH_2)_n$-A is linked to the cycle in position (a) or (b);
n is 0, 1, 2 or 3;
A represents a —$NR_3R_4$ group or a —$N^+R_3R_4R_5$ group;

R$_3$, R$_4$ and R$_5$ represent, independently of each other, a hydrogen atom, a (C$_1$-C$_{10}$)alkyl group, a (C$_1$-C$_{10}$) alkoxy group, a (C$_1$-C$_{10}$)alkyl-C(=NH)(—OH) group, a (C$_3$-C$_8$)cycloalkane group, a 6- to 10-membered aryl group or a 5- to 12-membered heteroaryl group; said alkyl or alkoxy groups being optionally substituted with one or more —NR$_6$R$_7$ group, —N$^+$R$_6$R$_7$R$_8$ group, (C$_3$-C$_8$)cycloalkane group, 6- to 10-membered aryl group or 5- to 12-membered heteroaryl group;

with R$_6$, R$_7$ and R$_8$ represent, independently of each other, a hydrogen atom or a (C$_1$-C$_6$)alkyl; and the compound of formula (I) contains at least one positive charged nitrogen atom;

provided that R$_1$ and R$_2$ are not both a hydrogen atom; and provided that when R$_1$ and R$_2$ are a methyl group, the group —(CH$_2$)$_n$-A is linked to the cycle in position (a), and n is 0, then A is not a group —N$^+$H$_3$.

2. Cationic compound according to claim 1, wherein R$_1$ and R$_2$ are chosen among a hydrogen atom or a methyl group.

3. Cationic compound according to claim 1, wherein the group —(CH$_2$)$_n$-A is linked to the cycle in position (a).

4. Cationic compound according to claim 1, wherein n is 0 or 1.

5. Cationic compound according to claim 1, wherein said compound is of formula (Ia):

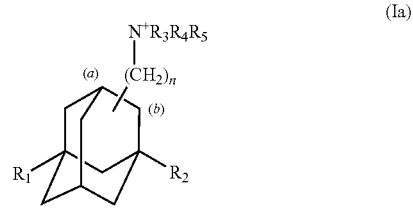

(Ia)

wherein R$_1$, R$_2$, R$_3$, R$_4$, R$_5$ and n are as defined in claim 1.

6. Cationic compound according to claim 1, wherein R$_3$, R$_4$ and R$_5$ represent, independently of each other, a (C$_1$-C$_{10}$) alkyl group.

7. Cationic compound according to claim 1, wherein at least one of R$_3$, R$_4$ and R$_5$ represents a methyl group.

8. Cationic compound according to claim 1, wherein R$_3$, R$_4$ and R$_5$ are simultaneously a methyl group.

9. Cationic compound according to claim 1, wherein R$_3$ and R$_4$ are a methyl group and R$_5$ represent a (C$_1$-C$_{10}$)alkyl group substituted with a (C$_3$-C$_8$)cycloalkane group.

10. Cationic compound according to claim 1, chosen among:

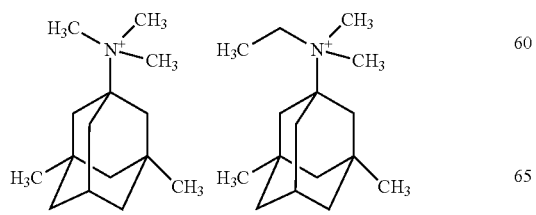

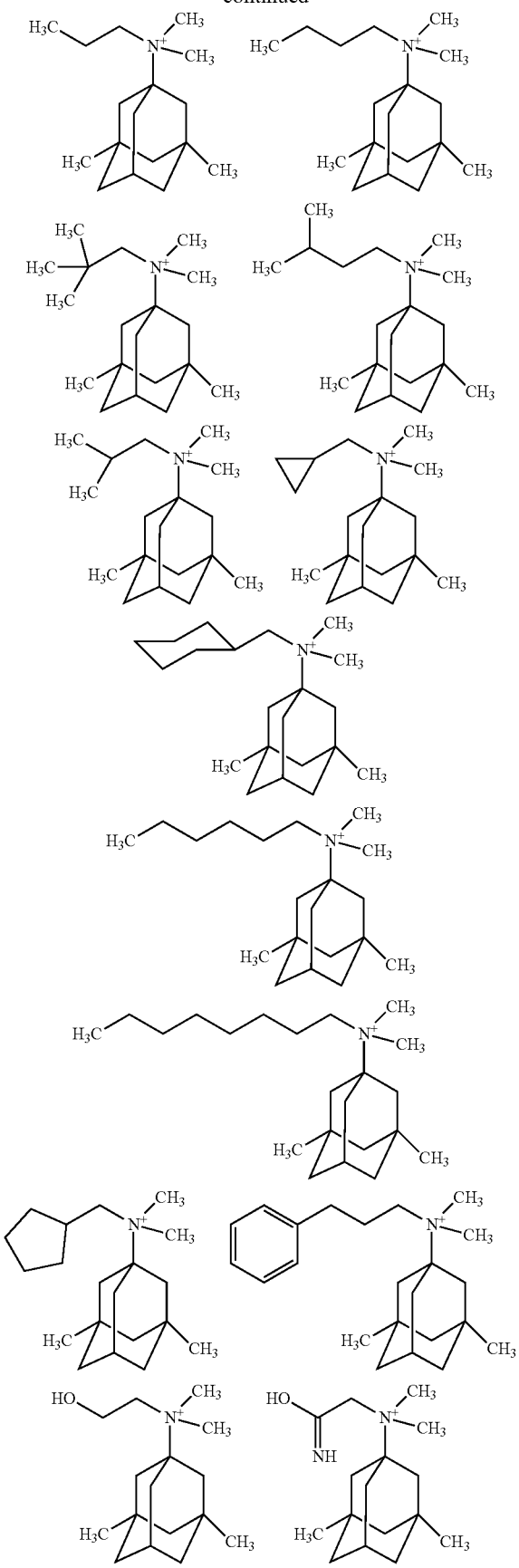

-continued

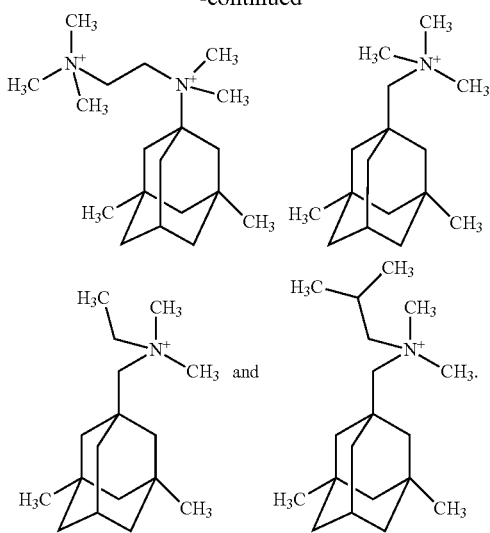

11. Medicament comprising as pharmaceutical active agent at least one compound as defined in claim 1.

12. A pharmaceutical composition comprising at least one compound as defined in claim 1, and at least one pharmaceutically acceptable excipient.

13. A pharmaceutical composition as claimed in claim 12, wherein said compound is in combination with at least one other therapeutic agent.

14. Cationic compound of formula (I) according to claim 1 for use as a peripheral NMDA receptor antagonist.

15. Cationic compound according to claim 1, for use for treating a disease or a condition chosen among pulmonary hypertension, pulmonary diseases involving inflammation, fibrosis and remodeling, non-neuronal cancers, diabetes, atherosclerosis, sickle cell disease, diseases involving thrombosis, acute infections, chronic infectious diseases, inflammatory disease, autoimmune disease, heart failure, arrhythmias, renal disorders, pain, psoriasis, atopic dermatitis, and osteoporosis.

16. Cationic compound according to claim 15, wherein the disease is pulmonary arterial hypertension.

* * * * *